(12) United States Patent
Ross

(10) Patent No.: US 7,485,713 B2
(45) Date of Patent: Feb. 3, 2009

(54) POLYPEPTIDES COMPRISING GROWTH HORMONE RECEPTOR EXTRACELLULAR DOMAIN AND GLYCOSYLPHOSPHATIDYLINOSITOL

(75) Inventor: Richard Ross, Sheffield (GB)

(73) Assignee: Asterion Limited, Sheffield (GB)

( * ) Notice: Subject to any disclaimer, the term of this patent is extended or adjusted under 35 U.S.C. 154(b) by 528 days.

(21) Appl. No.: 10/492,403

(22) PCT Filed: Oct. 11, 2002

(86) PCT No.: PCT/GB02/04665

§ 371 (c)(1),
(2), (4) Date: Apr. 13, 2004

(87) PCT Pub. No.: WO03/034275

PCT Pub. Date: Apr. 24, 2003

(65) Prior Publication Data

US 2005/0059577 A1    Mar. 17, 2005

(30) Foreign Application Priority Data

Oct. 13, 2001  (GB) ................. 0124620.6
Jan. 16, 2002  (GB) ................. 0200904.1
Aug. 14, 2002  (GB) ................. 0218889.4

(51) Int. Cl.
C07H 21/04   (2006.01)
C07K 14/71   (2006.01)
C07K 19/00   (2006.01)
C12N 15/12   (2006.01)
C12N 15/64   (2006.01)
C12N 15/63   (2006.01)
C12N 1/15    (2006.01)
C12N 1/11    (2006.01)
C12N 5/10    (2006.01)
A61K 38/17   (2006.01)

(52) U.S. Cl. .............. 536/23.4; 530/350; 435/69.1; 435/320.1; 435/254.2; 435/258.1; 435/348; 435/419; 435/325; 514/12

(58) Field of Classification Search ............. None
See application file for complete search history.

(56) References Cited

U.S. PATENT DOCUMENTS 4,857,637 A * 8/1989 Hammonds et al. ....... 424/185.1

(Continued)

FOREIGN PATENT DOCUMENTS

EP    976764 A    2/2000

(Continued)

OTHER PUBLICATIONS

NCBI Entrez Protein Locus P01831 (mouse Thy-1 protein), Jul. 21, 1986, 4 pages.*

(Continued)

Primary Examiner—Elizabeth C. Kemmerer
Assistant Examiner—Zachary C Howard
(74) Attorney, Agent, or Firm—Crowell & Moring LLP

(57) ABSTRACT

The present invention relates to polypeptides which comprise a receptor binding domain of a cytokine and a domain which includes a signal sequence for the attachment of glycosylphosphatidylinositol (GPI) anchors. The invention also relates to methods to manufacture the polypeptides, nucleic acids molecules encoding the polypeptides and therapeutic compositions comprising the polypeptides.

10 Claims, 25 Drawing Sheets

U.S. PATENT DOCUMENTS

| | | | | |
|---|---|---|---|---|
| 5,057,417 | A | * | 10/1991 | Hammonds et al. ......... 435/69.1 |
| 5,374,548 | A | * | 12/1994 | Caras .......................... 424/450 |
| 6,113,917 | A | * | 9/2000 | Fasel et al. ............... 424/268.1 |
| 2004/0052345 | A1 | * | 3/2004 | Kabeya ................... 379/93.09 |

FOREIGN PATENT DOCUMENTS

| | | |
|---|---|---|
| EP | 1081224 A1 * | 3/2001 |
| WO | 99/00423 | 1/1999 |
| WO | 00/56862 | 9/2000 |

OTHER PUBLICATIONS

NCBI Entrez Protein Locus P04216 (human Thy-1 protein), Mar. 20, 1987, 4 pages.*

Stevens et al. 2001. Biochimica et Biophysica Acta. 1511: 317-329.*

Phillips, A., J Pharm Pharmacology 53: 1169-1174, 2001.*

Wells (Sep. 18, 1990) Biochemistry 29(37): 8509-8517.*

Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*

Bork (2000) Genome Research 10:398.*

Skolnick and Fetrow (2000) Trends in Biotech. 18(1): 34.*

Doerks et al. (Jun. 1998) Trends in Genetics 14(6): 248.*

Smith and Zhang (Nov. 1997) Nature Biotechnology 15:1222.*

Brenner (Apr. 1999) Trends in Genetics 15(4): 132.*

Bork and Bairoch (Oct. 1996) Trends in Genetics 12(10): 425.*

Record for NCBI Entrez Protein Accession No. A33991. Mar. 23, 1990. 2 pages.*

Record for NCBI Entrez Protein Accession No. CAA27634. Feb. 16, 1995. 2 pages.*

R.J.M. Ross, "A Short Isoform of the Human Growth Hormone Receptor Functions as a Dominant Negative Inhibitor of the Full-Length Receptor and Generates Large Amounts of Binding Protein," Molecular Endocrinology, pp. 265-273.

Clive R. Da Costa, "Production of the Thyrotrophin Receptor Extracellular Domain as a Glycosylphosphatidylinositol-anchored Membrane Protein and its Interaction with Thyrotrophin and Autoantibodies," The Journal of Biological Chemistry, vol. 273, No. 19, pp. 11874-14798.

Mabrouka Maamra, "Studies with a Growth Hormone Antagonist and Dual-fluorescent Confocal Microscopy Demonstrate that the Full-length Human Growth Hormone Receptor, but Not the Truncated Isoform, is Very Rapidly Internalized Independent of Jak2-Stat5 Signaling," The Journal of Biological Chemistry, vol. 274, No. 21, pp. 14791-14798.

R. A. Meyers, "Molecular Biology and Biotechnology. A Comprehensive Desk Reference," VCH Publishers, pp. 200-204, pp. 392-397, pp. 474-476 and pp. 789-793.

* cited by examiner

FIGURE 1

```
          10        20        30        40        50
CAACTCAGTCCCACGTTTCGCGCGTTTCGGTGATGACGGTGAAAACCTCT 60        70        80        90       100
GACACATGCAGCTCCCGGAGACGGTCACAGCTTGTCTGTAAGCGGATGCC 110       120       130       140       150
GGGAGCAGACAAGCCCGTCAGGGCGCGTCAGCGGGTGTTGGCGGGTGTCG 160       170       180       190       200
GGGCTGGCTTAACTATGCGGCATCAGAGCAGATTGTACTGAGAGTGCACC 210       220       230       240       250
ATAATCCTTTTCATGGACATTGTATTATATGTGAGAATCGTTTACCCATA 260       270       280       290       300
AAGGGTAAAATTATTAATTTTTTTTTTTTTCAAATTTTAACGTTAAAGC 310       320       330       340       350
------GCAAATACCTTAATATCTGGATTTTTAATTTTTTTTGTAATTTA 360       370       380       390       400
AAAAATGATAATTAAAGTAATAATAAAAAATAAAAAAACAATTAAAAAAA 410       420       430       440       450
AAACCAATAGCCTATTGGTTTTATTTTTTTTTTTTTAAGGTCGGATAAAG 460       470       480       490       500
ATCAACAACCATTAAAAAAAAGTAATTAAATTTTATTATACATTTAAAT 510       520       530       540       550
ATTATTATTGTTATATTATTATTATTATTTTTATGTGAAGCACTTTCATC 560       570       580       590       600
ATGATTTAGAAACATTTTCTGTGGACAATTGATGGACCAGATTCATCATA 610       620       630       640       650
TTCTTCTTTTGAGATCCACATTTGTTGGAAAGTTGAGAGTGAAGCTAAAA 660       670       680       690       700
TAGATCCACCAATCCAGACAGAGTATTTACGTTCTGGTGGAGCAATGATT 710       720       730       740       750
TTAATTTTCATGGTTGATGGTGCTAAAGCAGTTAATTCTTTGTTCATACG 760       770       780       790       800
ATCAGCAATACCTGGGAACATAGTTGTACCACCTGATAAGACGACATTAC 810       820       830       840       850
CGTATAAATCTTTACGGATGATCCCTGTAATCCGGGCAGCGCAACGGAAC 860       870       880       890       900
ATTCATCAGTGTAAAAATGGAATCAATAAAGCCCTGCGCAGCGCGCAGGG 910       920       930       940       950
TCAGCCTGAATACGCGTTTAATGACCAGCACAGTCGTGATGGCAAGGTCA
```

FIGURE 1

```
              960       970       980       990      1000
        GAATAGCGCTGAGGTCTGCCTCGTGAAGAAGGTGTTGCTGACTCATACCA 1010      1020      1030      1040      1050
        GGCCTGAATCGCCCCATCATCCAGCCAGAAAGTGAGGGAGCCACGGTTGA 1060      1070      1080      1090      1100
        TGAGAGCTTTGTTGTAGGTGGACCAGTTGGTGATTTTGAACTTTTGCTTT 1110      1120      1130      1140      1150
        GCCACGGAACGGTCTGCGTTGTCGGGAAGATGCGTGATCTGATCCTTCAA 1160      1170      1180      1190      1200
        CTCAGCAAAAGTTCGATTTATTCAACAAAGCCGCCGTCCCGTCAAGTCAG 1210      1220      1230      1240      1250
        CGTAATGCTCTGCCAGTGTTACAACCAATTAACCAATTCTGATTAGAAAA 1260      1270      1280      1290      1300
        ACTCATCGAGCATCAAATGAAACTGCAATTTATTCATATCAGGATTATCA 1310      1320      1330      1340      1350
        ATACCATATTTTTGAAAAAGCCGTTTCTGTAATGAAGGAGAAAACTCACC 1360      1370      1380      1390      1400
        GAGGCAGTTCCATAGGATGGCAAGATCCTGGTATCGGTCTGCGATTCCGA 1410      1420      1430      1440      1450
        CTCGTCCAACATCAATACAACCTATTAATTTCCCCTCGTCAAAAATAAGG 1460      1470      1480      1490      1500
        TTATCAAGTGAGAAATCACCATGAGTGACGACTGAATCCGGTGAGAATGG 1510      1520      1530      1540      1550
        CAAAAGCTTATGCATTTCTTTCCAGACTTGTTCAACAGGCCAGCCATTAC 1560      1570      1580      1590      1600
        GCTCGTCATCAAAATCACTCGCATCAACCAAACCGTTATTCATTCGTGAT 1610      1620      1630      1640      1650
        TGCGCCTGAGCGAGACGAAATACGCGATCGCTGTTAAAAGGACAATTACA 1660      1670      1680      1690      1700
        AACAGGAATCGAATGCAACCGGCGCAGGAACACTGCCAGCGCATCAACAA 1710      1720      1730      1740      1750
        TATTTTCACCTGAATCAGGATATTCTTCTAATACCTGGAATGCTGTTTTC 1760      1770      1780      1790      1800
        CCGGGGATCGCAGTGGTGAGTAACCATGCATCATCAGGAGTACGGATAAA 1810      1820      1830      1840      1850
        ATGCTTGATGGTCGGAAGAGGCATAAATTCCGTCAGCCAGTTTAGTCTGA 1860      1870      1880      1890      1900
        CCATCTCATCTGTAACATCATTGGCAACGCTACCTTTGCCATGTTTCAGA
```

```
      1910        1920        1930        1940        1950
AACAACTCTGGCGCATCGGCTTCCCATACAATCGATAGATTGTCGCACC 1960        1970        1980        1990        2000
TGATTGCCCGACATTATCGCGAGCCCATTTATACCCATATAAATCAGCAT 2010        2020        2030        2040        2050
CCATGTTGGAATTTAATCGCGGCCTTGTTTTAAGAAATAAGAAAAAAAAA 2060        2070        2080        2090        2100
AAAAAAAAATCTTTTTATGCAATCTGAAAAAAAAAAAAAAAAAAAAAAAA 2110        2120        2130        2140        2150
AAAAAAAAAAAAAAAAAAAAAAATTTTTGAATCCCATTTTTTTI..TTAAT 2160        2170        2180        2190        2200
TTGGGTTTTAAAATTTTCAAATAATAATTAACCAACCCAAGTTTTTTTAA 2210        2220        2230        2240        2250
ACCATTTTTTTTTTTAAAGATTTGATGGGATTAATTAATTTGTAATCTAT 2260        2270        2280        2290        2300
TTAATTCAAAATAAATAAAAATAAATAAAAATTTTTTTTTATCGATCTCGA 2310        2320        2330        2340        2350
GACTAGAGAGGTTTATTTTTAAAAATTACAAAAACTAAAAAGAAAAATAA 2360        2370        2380        2390        2400
AAAGGAAAAATCTTATTAATCTGAAAATTACAGATTTGCCCCAATTTAAA 2410        2420        2430        2440        2450
GAAAAATTATCCAAAATAATCAATCAACAACGATATCTTTTTGATAGATA 2460        2470        2480        2490        2500
TTTATAAAAACTTTATCTTTTTTATTTTTTTCAAGTTGCGCAAAATAATAA 2510        2520        2530        2540        2550
AATTAAAATAAATATAAAAACTGTAAAAAGAAAAAAAAAAGTGTAAAGGT 2560        2570        2580        2590        2600
TTATTAATTATTTAATTATTATTCACTTTTTGTAATTATTTTTTTATTTT 2610        2620        2630        2640        2650
GAAGAATAATGATGGATATTTTATATAAAAAAAAAAAGAGATACTGAAAA 2660        2670        2680        2690        2700
AATAATAATTATAAAAAAAAAAAAAAAAATAGAATTTTAAAGTTTTAGT 2710        2720        2730        2740        2750
ACAAATGGATGATTTTTTTTTTTTTTTTTTTTTTTTTCCCAAATAATTCAA 2760        2770        2780        2790        2800
GTAATAACAACAAAGAACGGATATTCTGATGCCTAATTAAAAAAGAAATT 2810        2820        2830        2840        2850
TTTAAATAAAAAATGGGTTTTTTTTTAAGTAAAGTTATTTGAAATTGATTG
```

FIGURE 1

```
          2860       2870       2880       2890       2900
      AAATTTTCAAACCATGGGTGGTTTTTCGCTTTAAAATTGGGATTTTATTT 2910       2920       2930       2940       2950
      TTATTTTTTTATATTTTTTATTTTTTATTTTTTTTTTTTGAGGTTTCTG 2960       2970       2980       2990       3000
      AGATTATAAAATGAAATTTTTTTTTCTGATGCCTAATTAAAAAAGAAATT 3010       3020       3030       3040       3050
      TTTAAATAAAAAATGGCTTTTTTTTAAGTAAAGTTATTTGAAATCGATTG 3060       3070       3080       3090       3100
      AAATTTTCAAACCATGGGTGGTTTTTCGCTTTAAAATTGGGATTTTATTT 3110       3120       3130       3140       3150
      TTATTTTTTTATATTTTTTATTTTTTATTTTTTTTTTTTGAGGTTTCTG 3160       3170       3180       3190       3200
      AGATTATAAAATGAAATTTTTTTTTTTTTTTTAATTAATTCAAAAAAATA 3210       3220       3230       3240       3250
      ATCAAATAAATAAATATAATATAAAATGTCTAGATTTTTATTAGTATTGA
                                           F  L  L  V  L>
                                        ___CONTACT S___>

3260       3270       3280       3290       3300
      TAATATTATATAATATTTTAAATAGTGCACATTCAGCTCCAACCAGGAT
       I  I  L  Y  N  I  L  N  S  A  H  S  A  P>
      ___CONTACT SITE A SIGNAL PEPTIDE___>

3310       3320       3330       3340       3350
      CCAGGTACCATGTTAACGGAGCTGAATTCATCTCCAACTCCAACTGA 3360       3370       3380       3390       3400
      AACAGCCACCCCATCTCCAACTCCAAAACCAACAGCACACCAGAAGAAA 3410       3420       3430       3440       3450
      CTGAAGCACCTTCATCAGCAACAACTCTTATTTCACCATTATCTTTAATT 3460       3470       3480       3490       3500
      GTTATTTTCATTTCTTTTGTTTTAATTTAAGAGCTCGCTAGAGTCGT
                                      X 3510       3520       3530       3540       3550
      CCATCAATTGTTCACAGAAAATGTTTCTAAATTATTTAATAAATAATAAA 3560       3570       3580       3590       3600
      AAAACAAATTGTTGTAATAATCTAATATTTTCTTTTTTTTTTAATTTTTT 3610       3620       3630       3640       3650
      TTTTTTAAATCTTAATAATTATTAAGTTATTTTAATTTTTTTTTTTTTTT 3660       3670       3680       3690       3700
      TTTTTTTTTTTTTTTTTTTTTTTCTATCAAAAAAATCAAATATATTTAAAA 3710       3720       3730       3740       3750
      AATTTATTATTTACAGTACATTTTGAATGGTGAAGATAAATATATGCATT
```

FIGURE 1

```
          3760      3770      3780      3790      3800
   AGATGTAAAAGGCGACTGGTCGTCCATCAATTGTTCACAGAAAATGTTTC 3810      3820      3830      3840      3850
   TAAATTATTTAATAAATAATAAAAAAACAAATTGTTGTAATAATCTAATA 3860      3870      3880      3890      3900
   TTTTCTTTTTTTTTTTAATTTTTTTTTTTTAAATCTTAATAATTATTAAGT 3910      3920      3930      3940      3950
   TATTTTAATTTTTTTTTTTTTTTTTTTTTTTTTTTTTTTTTTTCTATC 3960      3970      3980      3990      4000
   AAAAAAATCAAATATATTTAAAAAATTTATTATTTACAGTACATTTTGAA 4010      4020      4030      4040      4050
   TGGTGAAGATAAATATATGCATTAGATGTAAAAGGGGACTCGAAAGCTTG 4060      4070      4080      4090      4100
   GCGTAATCATGGTCATAGCTGTTTCCTGTGTGAAATTGTTATCCGCTCAC 4110      4120      4130      4140      4150
   AATTCCACACAACATACGAGCCGGAAGCATAAAGTGTAAAGCCTGGGGTG 4160      4170      4180      4190      4200
   CCTAATGAGTGAGCTAACTCACATTAATTGCGTTGCGCTCACTGCCCGCT 4210      4220      4230      4240      4250
   TTCCAGTCGGGAAACCTGTCGTGCCAGCTGCATTAATGAATCGGCCAACG 4260      4270      4280      4290      4300
   CGCGGGGAGAGGCGGTTTGCGTATTGGGCGCTCTTCCGCTTCCTCGCTCA 4310      4320      4330      4340      4350
   CTGACTCGCTGCGCTCGGTCGTTCGGCTGCGGCGAGCGGTATCAGCTCAC 4360      4370      4380      4390      4400
   TCAAAGGCGGTAATACGGTTATCCACAGAATCAGGGGATAACGCAGGAAA 4410      4420      4430      4440      4450
   GAACATGTGAGCAAAAGGCCAGCAAAAGGCCAGGAACCGTAAAAAGGCCG 4460      4470      4480      4490      4500
   CGTTGCTGGCGTTTTTCCATAGGCTCCGCCCCCCTGACGAGCATCACAAA 4510      4520      4530      4540      4550
   AATCGACGCTCAAGTCAGAGGTGGCGAAACCCGACAGGACTATAAAGATA 4560      4570      4580      4590      4600
   CCAGGCGTTTCCCCCTGGAAGCTCCCTCGTGCGCTCTCCTGTTCCGACCC 4610      4620      4630      4640      4650
   TGCCGCTTACCGGATACCTGTCCGCCTTTCTCCCTTCGGGAAGCGTGGCG 4660      4670      4680      4690      4700
   CTTTCTCAATGCTCACGCTGTAGGTATCTCAGTTCGGTGTAGGTCGTTCG
```

```
       4710      4720      4730      4740      4750
CTCCAAGCTGGGCTGTGTGCACGAACCCCCGTTCAGCCCGACCGCTGCG 4760      4770      4780      4790      4800
CCTTATCCGGTAACTATCGTCTTGAGTCCAACCCGGTAAGACACGACTTA 4810      4820      4830      4840      4850
TCGCCACTGGCAGCAGCCACTGGTAACAGGATTAGCAGAGCGAGGTATGT 4860      4870      4880      4890      4900
AGGCGGTGCTACAGAGTTCTTGAAGTGGTGGCCTAACTACGGCTACACTA 4910      4920      4930      4940      4950
GAAGGACAGTATTTGGTATCTGCGCTCTGCTGAAGCCAGTTACCTTCGGA 4960      4970      4980      4990      5000
AAAAGAGTTGGTAGCTCTTGATCCGGCAAACAAACCACCGCTGGTAGCGG 5010      5020      5030      5040      5050
TGGTTTTTTTGTTTGCAAGCAGCAGATTACGCGCAGAAAAAAAGGATCTC 5060      5070      5080      5090      5100
AAGAAGATCCTTTGATCTTTTCTACGGGTCTGACGCTCAGTGGAACGAA 5110      5120      5130      5140      5150
AACTCACGTTAAGGGATTTTGGTCATGAGATTATCAAAAAGGATCTTCAC 5160      5170      5180      5190      5200
CTAGATCCTTTTAAATTAAAAATGAAGTTTTAAATCAATCTAAAGTATAT 5210      5220      5230      5240      5250
ATGAGTAAACTTGGTCTGACAGTTACCAATGCTTAATCTGTGAGGCACCT 5260      5270      5280      5290      5300
ATCTCAGCGATCTGTCTATTTCGTTCATCCATAGTTGCCTGACTCCCCGT 5310      5320      5330      5340      5350
CGTGTAGATAACTACGATACGGGAGGGCTTACCATCTGGCCCCAGTGCTG 5360      5370      5380      5390      5400
CAATGATACCGCGAGACCCACGCTCACCGGCTCCAGATTTATCAGCAATA 5410      5420      5430      5440      5450
AACCAGCCAGCCGGAAGGGCCGAGCGCAGAAGTGGTCCTGCAACTTTATC 5460      5470      5480      5490      5500
CGCCTCCATCCAGTCTATTAATTGTTGCCGGGAAGCTAGAGTAAGTAGTT 5510      5520      5530      5540      5550
CGCCAGTTAATAGTTTGCGCAACGTTGTTGCCATTGCTACAGGCATCGTG 5560      5570      5580      5590      5600
GTGTCACGCTCGTCGTTTGGTATGGCTTCATTCAGCTCCGGTTCCCAACG 5610      5620      5630      5640      5650
ATCAAGGCGAGTTACATGATCCCCCATGTTGTGCAAAAAAGCGGTTAGCT
```

FIGURE 1

```
          5660      5670      5680      5690      5700
     CCTTCGGTCCTCCGATCGTTGTCAGAAGTAAGTTGGCCGCAGTGTTATCA 5710      5720      5730      5740      5750
     CTCATGGTTATGGCAGCACTGCATAATTCTCTTACTGTCATGCCATCCGT 5760      5770      5780      5790      5800
     AAGATGCTTTTCTGTGACTGGTGAGTACTCAACCAAGTCATTCTGAGAAT 5810      5820      5830      5840      5850
     AGTGTATGCGGCGACCGAGTTGCTCTTGCCCGGCGTCAATACGGGATAAT 5860      5870      5880      5890      5900
     ACCGCGCCACATAGCAGAACTTTAAAAGTGCTCATCATTGGAAAACGTTC 5910      5920      5930      5940      5950
     TTCGGGGCGAAAACTCTCAAGGATCTTACCGCTGTTGAGATCCAGTTCGA 5960      5970      5980      5990      6000
     TGTAACCCACTCGTGCACCCAACTGATCTTCAGCATCTTTTACTTTCACC 6010      6020      6030      6040      6050
     AGCGTTTCTGGGTGAGCAAAAACAGGAAGGCAAAATGCCGCAAAAAAGGG 6060      6070      6080      6090      6100
     AATAAGGGCGACACGGAAATGTTGAATACTCATACTCTTCCTTTTTCAAT 6110      6120      6130      6140      6150
     ATTATTGAAGCATTTATCAGGGTTATTGTCTCATGAGCGGATACATATTT 6160      6170      6180      6190      6200
     GAATGTATTTAGAAAAATAAACAAATAGGGGTTCCGCGCACATTTCCCCG 6210      6220      6230      6240      6250
     AAAAGTGCCACCTGACGTCTAAGAAACCATTATTATCATGACATTAACCT 6260      6270      6280
     ATAAAAATAGGCGTATCACGAGGCCCTTTCGTC
```

FIGURE 1

Sequence Range: 1 to 6283

| Enzyme | #Cuts | Positions | | | | | |
|---|---|---|---|---|---|---|---|
| BamHI | 1 | 3297 | | | | | |
| BcoI | 2 | 1750 | 2296 | | | | |
| BglI | 1 | 5416 | | | | | |
| BscCI | 2 | 1667 | 1744 | | | | |
| BsiBI | 1 | 448 | | | | | |
| BsiLI | 10 | 762 | 999 | 1378 | 1735 | 3295 | 3302 |
| | | 4143 | 4431 | 4552 | 4565 | | |
| BsiXI | 3 | 1933 | 2291 | 3044 | | | |
| BsiZI | 7 | 584 | 1070 | 5338 | 5417 | 5434 | 5656 |
| | | 6272 | | | | | |
| ClaI | 3 | 1933 | 2291 | 3044 | | | |
| EcoRI | 1 | 3326 | | | | | |
| EcoRV | 1 | 2434 | | | | | |
| HindIII | 2 | 1504 | 4044 | | | | |
| HpaI | 1 | 3315 | | | | | |
| KpnI | 1 | 3308 | | | | | |
| NciI | 8 | 65 | 100 | 833 | 1751 | 1752 | 4783 |
| | | 5479 | 5830 | | | | |
| NcoI | 3 | 2862 | 3062 | 3308 | | | |
| NruI | 1 | 1969 | | | | | |
| PvuII | 1 | 4227 | | | | | |
| RsaI | 8 | 186 | 777 | 1791 | 2700 | 3306 | 3717 |
| | | 3990 | 5776 | | | | |
| SacI | 2 | 3324 | 3488 | | | | |
| SmaI | 1 | 1752 | | | | | |
| StuI | 1 | 1002 | | | | | |
| XbaI | 1 | 3229 | | | | | |
| XhoI | 1 | 2296 | | | | | |

FIGURE 1

BglII
BsiCI
BsiMI
BsiQI
NotI
PstI
SacII
SalI
SfiI
SpeI
SphI

FIGURE 2

```
cag gat cca TTT
TCTGGAAGTG AGGCCACAGC AGCTATCCTT AGCAGAGCAC CCTGGAGTCT
GCAAAGTGTT AATCCAGGCC TAAAGACAAA TTCTTCTAAG GAGCCTAAAT
TCACCAAGTG CCGTTCACCT GAGCGAGAGA CTTTTTCATG CCACTGGACA
GATGAGGTTC ATCATGGTAC AAAGAACCTA GGACCCATAC AGCTGTTCTA
TACCAGAAGG AACACTCAAG AATGGACTCA AGAATGGAAA GAATGCCCTG
ATTATGTTTC TGCTGGGGAA AACAGCTGTT ACTTTAATTC ATCGTTTACC
TCCATCTGGA TACCTTATTG TATCAAGCTA ACTAGCAATG GTGGTACAGT
GGATGAAAAG TGTTTCTCTG TTGATGAAAT AGTGCAACCA GATCCACCCA
TTGCCCTCAA CTGGACTTTA CTGAACGTCA GTTTAACTGG GATTCATGCA
GATATCCAAG TGAGATGGGA AGCACCACGC AATGCAGATA TTCAGAAAGG
ATGGATGGTT CTGGAGTATG AACTTCAATA CAAAGAAGTA AATGAAACTA
AATGGAAAAT GATGGACCCT ATATTGACAA CATCAGTTCC AGTGTACTCA
TTGAAAGTGG ATAAGGAATA TGAAGTACGC GTGAGATCCA AACAACGAAA
CTCTGGAAAT TATGGCGAGT TCAGTGAGGT GCTCTATGTA ACACTTCCTC
AGATGAGCCA ATTTACATGT GAAGAAGATT CTAC cga att cca
```

FIGURE 3

```
  1  TTTTCTGGAA GTGAGGCCAC AGCAGCTATC CTTAGCAGAG CACCCTGGAG
 51  TCTGCAAAGT GTTAATCCAG GCCTAAAGAC AAATTCTTCT AAGGAGCCTA
101  AATTCACCAA GTGCCGTTCA CCTGAGCGAG AGACTTTTTC ATGCCACTGG
151  ACAGATGAGG TTCATCATGG TACAAAGAAC CTAGGACCCA TACAGCTGTT
201  CTATACCAGA AGGAACACTC AAGAATGGAC TCAAGAATGG AAAGAATGCC
251  CTGATTATGT TTCTGCTGGG GAAAACAGCT GTTACTTTAA TTCATCGTTT
301  ACCTCCATCT GGATACCTTA TTGTATCAAG CTAACTAGCA ATGGTGGTAC
351  AGTGGATGAA AAGTGTTTCT CTGTTGATGA AATAGTGCAA CCAGATCCAC
401  CCATTGCCCT CAACTGGACT TTACTGAACG TCAGTTTAAC TGGGATTCAT
451  GCAGATATCC AAGTGAGATG GGAAGCACCA CGCAATGCAG ATATTCAGAA
501  AGGATGGATG GTTCTGGAGT ATGAACTTCA ATACAAAGAA GTAAATGAAA
551  CTAAATGGAA AATGATGGAC CCTATATTGA CAACATCAGT TCCAGTGTAC
601  TCATTGAAAG TGGATAAGGA ATATGAAGTA CGCGTGAGAT CCAAACAACG
651  AAACTCTGGA AATTATGGCG AGTTCAGTGA GGTGCTCTAT GTAACACTTC
701  CTCAGATGAG CCAATTTACA TGTGAAGAAG ATTTCTACcg aattccaTct
751  ccaactccaa ctgaaacagc caccccatct ccaactccaA aaccaaccag
801  cacaccagaa gaaactgaag caccttcatc agcaAcaact cttatttcac
851  cattatcttt aattgttatt ttcattTctt ttgttttatt aatttaa
```

```
  1  FSGSEATAAI LSRAPWSLQS VNPGLKTNSS KEPKFTKCRS PERETFSCHW
 51  TDEVHHGTKN LGPIQLFYTR RNTQEWTQEW KECPDYVSAG ENSCYFNSSF
101  TSIWIPYCIK LTSNGGTVDE KCFSVDEIVQ PDPPIALNWT LLNVSLTGIH
151  ADIQVRWEAP RNADIQKGWM VLEYELQYKE VNETKWKMMD PILTTSVPVY
201  SLKVDKEYEV RVRSKQRNSG NYGEFSEVLY VTLPQMSQFT CEEDFYRIPS
251  PTPTETATPS PTPKPTSTPE ETEAPSSATT LISPLSLIVI FISFVLLI*
```

FIGURE 8

```
   1 GCGCGCGTTG ACATTGATTA TTGACTAGTT ATTAATAGTA ATCAATTACG GGGTCATTAG
  61 TTCATAGCCC ATATATGGAG TTCCGCGTTA CATAACTTAC GGTAAATGGC CCGCCTGGCT
 121 GACCGCCCAA CGACCCCCGC CCATTGACGT CAATAATGAC GTATGTTCCC ATAGTAACGC
 181 CAATAGGGAC TTTCCATTGA CGTCAATGGG TGGACTATTT ACGGTAAACT GCCCACTTGG
 241 CAGTACATCA AGTGTATCAT ATGCCAAGTA CGCCCCCTAT TGACGTCAAT GACGGTAAAT
 301 GGCCCGCCTG GCATTATGCC CAGTACATGA CCTTATGGGA CTTTCCTACT TGGCAGTACA
 361 TCTACGTATT AGTCATCGCT ATTACCATGG TGATGCGGTT TTGGCAGTAC ATCAATGGGC
 421 GTGGATAGCG GTTTGACTCA CGGGGATTTC CAAGTCTCCA CCCCATTGAC GTCAATGGGA
 481 GTTTGTTTTG GCACCAAAAT CAACGGGACT TTCCAAAATG TCGTAACAAC TCCGCCCCAT
 541 TGACGCAAAT GGGCGGTAGG CGTGTACGGT GGGAGGTCTA TATAAGCAGA GCTCTCTGGC
 601 TAACTAGAGA ACCCACTGCT TACTGGCTTA TCGAAATTAA TACGACTCAC TATAGGGAGA
 661 CCCAAGCTTG GTACCGAGCT CGGATCCACT AGTAACGGCC GCCAGTGTGC TGGAATTCTG
 721 CAGATATCGA CAAGCTGGTC AAGTGTGGCG GCATAAGCCT GCTGGTTCAG AACACATCCT
 781 GGATGCTGCT GCTGCTGCTT TCCCTCTCCC TCCTCCAAGC CCTAGACTTC ATTTCTCTGT
 841 GACTCGAGCA TGCATCTAGA GGGCCCTATT CTATAGTGTC ACCTAAATGC TAGAGCTCGC
 901 TGATCAGCCT CGACTGTGCC TTCTAGTTGC CAGCCATCTG TTGTTTGCCC CTCCCCCGTG
 961 CCTTCCTTGA CCCTGGAAGG TGCCACTCCC ACTGTCCTTT CCTAATAAAA TGAGGAAATT
1021 GCATCGCATT GTCTGAGTAG GTGTCATTCT ATTCTGGGGG GTGGGGTGGG GCAGGACAGC
1081 AAGGGGGAGG ATTGGGAAGA CAATAGCAGG CATGCTGGGG ATGCGGTGGG CTCTATGGCT
1141 TCTGAGGCGG AAAGAACCAG TGGCGGTAAT ACGGTTATCC ACAGAATCAG GGGATAACGC
1201 AGGAAAGAAC ATGTGAGCAA AAGGCCAGCA AAAGGCCAGG AACCGTAAAA AGGCCGCGTT
1261 GCTGGCGTTT TTCCATAGGC TCCGCCCCCC TGACGAGCAT CACAAAAATC GACGCTCAAG
1321 TCAGAGGTGG CGAAACCCGA CAGGACTATA AAGATACCAG GCGTTTCCCC CTGGAAGCTC
1381 CCTCGTGCGC TCTCCTGTTC CGACCCTGCC GCTTACCGGA TACCTGTCCG CCTTTCTCCC
1441 TTCGGGAAGC GTGGCGCTTT CTCATAGCTC ACGCTGTAGG TATCTCAGTT CGGTGTAGGT
1501 CGTTCGCTCC AAGCTGGGCT GTGTGCACGA ACCCCCCGTT CAGCCCGACC GCTGCGCCTT
1561 ATCCGGTAAC TATCGTCTTG AGTCCAACCC GGTAAGACAC GACTTATCGC CACTGGCAGC
1621 AGCCACTGGT AACAGGATTA GCAGAGCGAG GTATGTAGGC GGTGCTACAG AGTTCTTGAA
1681 GTGGTGGCCT AACTACGGCT ACACTAGAAG GACAGTATTT GGTATCTGCG CTCTGCTGAA
1741 GCCAGTTACC TTCGAAAAAA GAGTTGGTAG CTCTTGATCC GGCAAACAAA CCACCGCTGG
1801 TAGCGGTGGT TTTTTTGTTT GCAAGCAGCA GATTACGCGC AGAAAAAAAG GATCTCAAGA
1861 AGATCCTTTG ATCTTTTCTA CGGGGTCTGA CGCTCAGTGG AACGAAAACT CACGTTAAGG
1921 GATTTTGGTC ATGAGATTAT CAAAAAGGAT CTTCACCTAG ATCCTTTTAA ATTAAAAATG
1981 AAGTTTTAAA TCAATCTAAA GTATATATGA GTAACCTGAG CTATGGCAG GGCCTGCCGC
2041 CCCGACGTTG GCTGCGAGCC CTGGGCCTTC ACCCGAACTT GGGGGGTGGG GTGGGGAAAA
2101 GGAAGAAACG CGGGCGTATT GGCCCCAATG GGGTCTCGGT GGGGTATCGA CAGAGTGCCA
2161 GCCCTGGGAC CGAACCCCGC GTTTATGAAC AAACGACCCA ACACCGTGCG TTTTATTCTG
2221 TCTTTTTATT GCCGTCATAG CGCGGGTTCC TTCCGGTATT GTCTCCTTCC GTGTTTCAGT
2281 TAGCCTCCCC CTAGGGTGGG CGAAGAACTC CAGCATGAGA TCCCCGCGCT GGAGGATCAT
2341 CCAGCCGGCG TCCCGGAAAA CGATTCCGAA GCCCAACCTT TCATAGAAGG CGGCGGTGGA
2401 ATCGAAATCT CGTGATGGCA GGTTGGGCGT CGCTTGGTCG GTCATTTCGA ACCCCAGAGT
2461 CCCGCTCAGA AGAACTCGTC AAGAAGGCGA TAGAAGGCGA TGCGCTGCGA ATCGGGAGCG
2521 GCGATACCGT AAAGCACGAG GAAGCGGTCA GCCCATTCGC CGCCAAGCTC TTCAGCAATA
2581 TCACGGGTAG CCAACGCTAT GTCCTGATAG CGGTCCGCCA CACCCAGCCG GCCACAGTCG
2641 ATGAATCCAG AAAAGCGGCC ATTTTCCACC ATGATATTCG GCAAGCAGGC ATCGCCATGG
2701 GTCACGACGA GATCCTCGCC GTCGGGCATG CTCGCCTTGA GCCTGGCGAA CAGTTCGGCT
2761 GGCGCGAGCC CCTGATGCTC TTGATCATCC TGATCGACAA GACCGGCTTC CATCCGAGTA
2821 CGTGCTCGCT CGATGCGATG TTTCGCTTGG TGGTCGAATG GCAGGTAGC CGGATCAAGC
2881 GTATGCAGCC GCCGCATTGC ATCAGCCATG ATGGATACTT TCTCGGCAGG AGCAAGGTGA
2941 GATGACAGGA GATCCTGCCC CGGCACTTCG CCCAATAGCA GCCAGTCCCT TCCCGCTTCA
3001 GTGACAACGT CGAGCACAGC TGCGCAAGGA ACGCCCGTCG TGGCCAGCCA CGATAGCCGC
3061 GCTGCCTCGT CTTGCAGTTC ATTCAGGGCA CCGGACAGGT CGGTCTTGAC AAAAAGAACC
3121 GGGCGCCCCT GCGCTGACAG CCGGAACACG GCGGCATCAG AGCAGCCGAT TGTCTGTTGT
3181 GCCCAGTCAT AGCCGAATAG CCTCTCCACC CAAGCGGCCG GAGAACCTGC GTGCAATCCA
3241 TCTTGTTCAA TCATGCGAAA CGATCCTCAT CCTGTCTCTT GATCGATCTT TGCAAAAGCC
3301 TAGGCCTCCA AAAAAGCCTC CTCACTACTT CTGGAATAGC TCAGAGGCCG AGGCGGCCTC
3361 GGCCTCTGCA TAAATAAAAA AAATTAGTCA GCCATGGGGC GGAGAATGGG CGGAACTGGG
3421 CGGAGTTAGG GGCGGGATGG GCGGAGTTAG GGGCGGGACT ATGGTTGCTG ACTAATTGAG
```

FIGURE 8 (continued)

```
3481 ATGCATGCTT TGCATACTTC TGCCTGCTGG GGAGCCTGGG GACTTTCCAC ACCTGGTTGC
3541 TGACTAATTG AGATGCATGC TTTGCATACT TCTGCCTGCT GGGGAGCCTG GGGACTTTCC
3601 ACACCCTAAC TGACACACAT TCCACAGCTG GTTCTTTCCG CCTCAGGACT CTTCCTTTTT
3661 CAATAAATCA ATCTAAAGTA TATATGAGTA AACTTGGTCT GACAGTTACC AATGCTTAAT
3721 CAGTGAGGCA CCTATCTCAG CGATCTGTCT ATTTCGTTCA TCCATAGTTG CCTGACTCCC
3781 CGTCGTGTAG ATAACTACGA TACGGGAGGG CTTACCATCT GGCCCCAGTG CTGCAATGAT
3841 ACCGCGAGAC CCACGCTCAC CGGCTCCAGA TTTATCAGCA ATAAACCAGC CAGCCGGAAG
3901 GGCCGAGCGC AGAAGTGGTC CTGCAACTTT ATCCGCCTCC ATCCAGTCTA TTAATTGTTG
3961 CCGGAAGCT AGAGTAAGTA GTTCGCCAGT TAATAGTTTG CGCAACGTTG TTGCCATTGC
4021 TACAGGCATC GTGGTGTCAC GCTCGTCGTT TGGTATGGCT TCATTCAGCT CCGGTTCCCA
4081 ACGATCAAGG CGAGTTACAT GATCCCCCAT GTTGTGCAAA AAAGCGGTTA GCTCCTTCGG
4141 TCCTCCGATC GTTGTCAGAA GTAAGTTGGC CGCAGTGTTA TCACTCATGG TTATGGCAGC
4201 ACTGCATAAT TCTCTTACTG TCATGCCATC CGTAAGATGC TTTTCTGTGA CTGGTGAGTA
4261 CTCAACCAAG TCATTCTGAG AATAGTGTAT GCGGCGACCG AGTTGCTCTT GCCCGGCGTC
4321 AATACGGGAT AATACCGCGC CACATAGCAG AACTTTAAAA GTGCTCATCA TTGGAAAACG
4381 TTCTTCGGGG CGAAAACTCT CAAGGATCTT ACCGCTGTTG AGATCCAGTT CGATGTAACC
4441 CACTCGTGCA CCCAACTGAT CTTCAGCATC TTTTACTTTC ACCAGCGTTT CTGGGTGAGC
4501 AAAAACAGGA AGGCAAAATG CCGCAAAAAA GGGAATAAGG GCGACACGGA AATGTTGAAT
4561 ACTCATACTC TTCCTTTTTC AATATTATTG AAGCATTTAT CAGGGTTATT GTCTCATGAG
4621 CGGATACATA TTTGAATGTA TTTAGAAAAA TAAACAAATA GGGGTTCCGC GCACATTTCC
4681 CCGAAAAGTG CCACCTGACG CGCCCTGTAG CGGCGCATTA AGCGCGGCGG GTGTGGTGGT
4741 TACGCGCAGC GTGACCGCTA CACTTGCCAG CGCCCTAGCG CCCGCTCCTT TCGCTTTCTT
4801 CCCTTCCTTT CTCGCCACGT TCGCCGGCTT TCCCCGTCAA GCTCTAAATC GGGGGCTCCC
4861 TTTAGGGTTC CGATTTAGTG CTTTACGGCA CCTCGACCCC AAAAAACTTG ATTAGGGTGA
4921 TGGTTCACGT AGTGGGCCAT CGCCCTGATA GACGGTTTTT CGCCCTTTGA CGTTGGAGTC
4981 CACGTTCTTT AATAGTGGAC TCTTGTTCCA AACTGGAACA ACACTCAACC CTATCTCGGT
5041 CTATTCTTTT GATTTATAAG GGATTTTGCC GATTTCGGCC TATTGGTTAA AAAATGAGCT
5101 GATTTAACAA AAATTTAACG CGAATTTTAA CAAAATATTA ACGCTTACAA TTTAC
```

Figure 9

```
     601 TAACTAGAGA ACCCACTGCT TACTGGCTTA TCGAAATTAA TACGACTCAC TATAGGGAGA
     661 CCCAAGCTTG GTACCGAGCT CG (BamHI in bold)
gatcctctagactcgaggtcctacaggt (sequence from original GHR vector)
atggatctctggcagctgctgttgaccttggcactggcaggatcaagtgatgct (GHR signal)
ttttctggaagtgaggccacagcagctatccttagcagagcacoctggagtctgcaaagtgttaatccaggcctaaagac
aaattcttctaaggagcctaaattcaccaagtgccgttcacctgagcgagagactttttcatgccactggacagatgagg
ttcatcatggtacaaagaacctaggacccatacagctgttctataccagaaggaacactcaagaatggactcaagaatgg
aaagaatgccctgattatgtttctgctggggaaaacagctgttactttaattcatcgtttacctccatctggatacctta
ttgtatcaagctaactagcaatggtggtacagtggatgaaaagtgtttctctgttgatgaaatagtgcaaccagatccac
ccattgccctcaactggactttactgaacgtcagtttaactgggattcatgcagatatccaagtgagatgggaagcacca
cgcaatgcagatattcagaaaggatggatggttctggagtatgaacttcaatacaaagaagtaaatgaaactaaatggaa
aatgatggacccatattgacaacatcagttccagtgtactcattgaaagtggataaggaatatgaagtgcgtgtgagat
ccaaacaacgaaactctggaaattatggcgagttcagtgaggtgctctatgtaacacttcctcagatgagccaatttaca
tgtgaagaagatttctac (GHR extracellular domain)
GGG (inserted codon to keep in frame and generate EcoRI site in bold)
AAT TCT G.
     721 CA GAT ATC GAC AAG CTG GTC AAG TGT GGC G GCATAAGCCT GCTGGTTCAG
```

```
  1  RIL*TRGPTG MDLWQLLLTL ALAGSSDAFS GSEATAAILS RAPWSLQSVN

51  PGLKTNSSKE PKFTKCRSPE RETFSCHWTD EVHHGTKNLG PIQLFYTRRN

101  TQEWTQEWKE CPDYVSAGEN SCYFNSSFTS IWIPYCIKLT SNGGTVDEKC

151  FSVDEIVQPD PPIALNWTLL NVSLTGIHAD IQVRWEAPRN ADIQKGWMVL

201  EYELQYKEVN ETKWKMMDPI LTTSVPVYSL KVDKEYEVRV RSKQRNSGNY

251  GEFSEVLYVT LPQMSQFTCE EDFYGNSADI DKLVKCGGIS LLVQNTSWML

301  LLLLSLSLLQ ALDFISL*LE HASRGPYSIV SPKC*SSLIS LDCAF*LPAI

351  CCLPLPRAFL DPGRCHSHCP FLIK*GNCIA LSE*VSFYSG GWGGAGQ
```

FIGURE 12

| sample number | date | cells | tranfection | GHBP (pM) |
|---|---|---|---|---|
| 1 | 29/5/02. | CHO cells | pcdna3 | <70 |
| 2 | 29/5/02. | CHO cells | GHRfl | 93 |
| 5 | 6/6/02. | CHO cells | pcdna3 | <70 |
| 6 | 6/6/02. | CHO cells | GHRfl | 408 |
| 9 | 13/6/02. | CHO cells | pcdna3 | <70 |
| 10 | 13/6/02. | CHO cells | GHRfl | <70 |
| 13 | 29/5/02. | HI cells | no | 192 |
| 14 | 6/6/02. | HI cells | no | 455 |
| 15 | 13/6/02. | HI cells | no | 171 |
| 16 | 3/8/01. | 293cells | no | <70 |
| 17 | 3/8/01. | 293cells | GHRfl | 193 |
| 20 | 18/7/02. | CHO cells | pcdna3 | <70 |
| 21 | 18/7/02. | CHO cells | GHRfl | 752 |
| 22 | 18/7/02. | CHO cells | GHR-GPI | >8000 |
| 23 | 18/7/02. | HI cells | no | 72 | pcDNA3 cells transfected with vector only
GHRfl cells transfected with wild-type GH reptor
HI cells — stable clone 293 cells expressing wild-type GH receptor
GHR-GPI cells transfected with GHR linked to GPI

FIGURE 13

```
  1 mglstvpdll lplvllellv giypsgvigl vphlgdrekr dsvcpqgkyi hpqnnsicct
 61 kchkgtylyn dcpgpgqdtd crecesgsft asenhlrhcl scskcrkemg qveissctvd
121 rdtvcgcrkn qyrhywsenl fqcfncslcl ngtvhlscqe kqntvctcha gfflrenecv
181 scsnckksle ctklclpqie nvkgtedsgt tvllplviff glcllsllfi glmyryqrwk
241 sklysivcgk stpekegele gtttkplapn psfsptpgft ptlgfspvps stftssstyt
301 pgdcpnfaap rrevappyqg adpilatala sdpipnplqk wedsahkpqs ldtddpatly
361 avvenvpplr wkefvrrlgl sdheidrlel qngrclreaq ysmlatwrrr tprreatlel
421 lgrvlrdmdl lgcledieea lcgpaalppa psllr
```

```
   1 cggcccagtg atcttgaacc ccaaaggcca gaactggagc ctcagtccag agaattctga
  61 gaaaattaaa gcagagagga ggggagagat cactgggacc aggccgtgat ctctatgccc
 121 gagtctcaac cctcaactgt caccccaagg cacttgggac gtcctggaca gaccgagtcc
 181 cgggaagccc cagcactgcc gctgccacac tgccctgagc ccaaatgggg gagtgagagg
                                                    MetGl yLeuSer...
 241 ccatagctgt ctggcatggg cctctccacc gtgcctgacc tgctgctgcc gctggtgctc
                                 Il eTyrProSer...
 301 ctggagctgt tggtgggaat ataccCctca ggggttattg gactggtccc tcacctaggg
 361 gacagggaga agagagatag tgtgtgtccc caaggaaaat atatccaccc tcaaaataat
 421 tcgatttgct gtaccaagtg ccacaaagga acctacttgt acaatgactg tccaggcccg
 481 gggcaggata cggactgcag ggagtgtgag agcggctcct tcaccgcttc agaaaaccac
 541 ctcagacact gcctcagctg ctccaaatgc cgaaaggaaa tgggtcaggt ggagatctct
 601 tcttgcacag tggaccggga caccgtgtgt ggctgcagga agaaccagta ccggcattat
 661 tggagtgaaa acctttttcca gtgcttcaat tgcagcctct gcctcaatgg gaccgtgcac
 721 ctctcctgcc aggagaaaca gaacaccgtg tgcacctgcc atgcaggttt ctttctaaga
 781 gaaaacgagt gtgtctcctg tagtaactgt aagaaaagcc tggagtgcac gaagttgtgc
                                                            Va lLeuLeuPro
 841 ctaccccaga ttgagaatgt taagggcact gaggactcag gcaccacagt gctgttgccc
 901 ctggtcattt tctttggtct ttgccttttca tccctcctct tcattggttt aatgtatcgc
 961 taccaacggt ggaagtccaa gctctactcc attgtttgtg ggaaatcgac acctgaaaaa
1021 gagggggagc ttgaaggaac tactactaag cccctggccc caaaccaag cttcagtccc
1081 actccaggct tcaccCccac cctgggcttc agtcccgtgc ccagttccac cttcacctcc
1141 agctccacct ataccCccgg tgactgtccc aactttgcgg ctccccgcag agaggtggca
1201 ccacctatc aggggctga cccCatcctt gcgacagccc tcgcctccga cccCatcccc
1261 aacccCcttc agaagtggga ggacagcgcc cacaagccac agagcctaga cactgatgac
1321 cccgcgacgc tgtacgccgt ggtggagaac gtgccCccgt tgcgctggaa ggaattcgtg
1381 cggcgcctag ggctgagcga ccacgagatc gatcggctgg agctgcagaa cgggcgctgc
1441 ctgcgcgagg cgcaatacag catgctggcg acctggaggc ggcgcacgcc gcggcgcgag
1501 gccacgctgg agctgctggg acgcgtgctc cgcgacatgg acctgctggg ctgcctggag
1561 gacatcgagg aggcgctttg cggccccgcc gccctcccgc ccgcgcccag tcttctcaga
1621 tgaggctgcg ccctgcgggg cagctctaag gaccgtcctg cgagatcgcc ttccaacccc
1681 actttttct ggaaaggagg ggtcctgcag gggcaagcag gagctagcag ccgcctactt
1741 ggtgctaacc cctcgatgta catagctttt ctcagctgcc tgcgcgccgc cgacagtcag
1801 cgctgtgcgc gcggagagac gtgcgccgtg ggctcaagag cctgagtggg tggtttgcga
1861 ggatgaggga cgctatgcct catgcccgtt ttgggtgtcc tcaccagcaa ggctgctcgg
1921 gggcccctgg ttcgtccctg agccttttc acagtgcata agcagttttt tttgtttttg
1981 ttttgttttg ttttgttttt aaatcaatca tgttacacta atagaaactt ggcactcctg
2041 tgccctctgc ctggacaagc acatagcaag ctgaactgtc ctaaggcagg ggcgagcacg
2101 gaacaatggg gccttcagct ggagctgtgg acttttgtac atacactaaa attctgaagt
2161 t
```

FIGURE 14

RIL*TRGPTG mglstvpdll lplvllellv giypsgvigl vphlgdrekr dsvcpqgkyi
hpqnnsicct kchkgtylyn dcpgpgqdtd crecesgsft asenhlrhcl scskcrkemg
qveissctvd rdtvcgcrkn qyrhywsenl fqcfncslcl ngtvhlscqe kqntvctcha
gfflrenecv scsnckksle ctklclpqie nvkgtedsgt tGNSADI DKLVKCGGIS
LLVQNTSWML LLLLSLSLLQ ALDFISL*LE HASRGPYSIV SPKC*SSLIS LDCAF*LPAI
CCLPLPRAFL DPGRCHSHCP FLIK*GNCIA LSE*VSFYSG GWGGAGQ

FIGURE 15

```
  1  MICQKFCVVL  LHWEFIYVIT  AF NLSYPITP  WRFKLSCMPP  NSTYDYFLLP
 51  AGLSKNTSNS  NGHYETAVEP  KFNSSGTHFS  NLSKTTFHCC  FRSEQDRNCS
101  LCADNIEGKT  FVSTVNSLVF  QQIDANWNIQ  CWLKGDLKLF  ICYVESLFKN
151  LFRNYNYKVH  LLYVLPEVLE  DSPLVPQKGS  FQMVHCNCSV  HECCECLVPV
201  PTAKLNDTLL  MCLKITSGGV  IFQSPLMSVQ  PINMVKPDPP  LGLHMEITDD
251  GNLKISWSSP  PLVPFPLQYQ  VKYSENSTTV  IREADKIVSA  TSLLVDSILP
301  GSSYEVQVRG  KRLDGPGIWS  DWSTPRVFTT  QDVIYFPPKI  LTSVGSNVSF
351  HCIYKKENKI  VPSKEIVWWM  NLAEKIPQSQ  YDVVSDHVSK  VTFFNLNETK
401  PRGKFTYDAV  YCCNEHECHH  RYAELYVIDV  NINISCETDG  YLTKMTCRWS
451  TSTIQSLAES  TLQLRYHRSS  LYCSDIPSIH  PISEPKDCYL  QSDGFYECIF
501  QPIFLLSGYT  MWIRINHSLG  SLDSPPTCVL  PDSVVKPLPP  SSVKAEITIN
551  IGLLKISWEK  PVFPENNLQF  QIRYGLSGKE  VQWKMYEVYD  AKSKSVSLPV
601  PDLCAVYAVQ  VRCKRLDGLG  YWSNWSNPAY  TVVMDIKVPM  RGPEFWRIIN
651  GDTMKKEKNV  TLLWKPLMKN  DSLCSVQRYV  INHHTSCNGT  WSEDVGNHTK
701  FTFLWTEQAH  TVTVLAINSI  GASVANFNLT  FSWPMSKVNI  VQSLSAYPLN
751  SSCVIVSWIL  SPSDYKLMYF  IIEWKNLNED  GEIKWLRISS  SVKKYYIHDH
801  FIPIEKYQFS  LYPIFMEGVG  KPKIINSFTQ  DDIEKHQS GN  SADIDKLVKC
851  GGISLLVQNT  SWMLLLLLSL  SLLQALDFIS  L*LEHASRGP  YSIVSPKC*S
901  SLISLDCAF*  LPAICCLPLP  RAFLDPGR
```

FIGURE 16

Cytokines and accession numbers.

| Cytokine | Accession Number |
|---|---|
| Homo sapiens growth hormone (GH) | XM_044413; XM_044403 |
| Homo sapiens leptin | U43168 |
| Homo sapiens erythropoietin (EPO) | XM_011627 |
| Gallus gallus prolactin | AF288765 |
| Homo sapiens tumor necrosis factor (TNF) | XM_041847; XM_011402 |
| Homo sapiens interleukin 2 (IL2) | XM_035510; XM_035509; XM_035511 |
| Homo sapiens interleukin 3 (IL3) | XM_029116; XM_029114; XM_003752 |
| Homo sapiens interleukin 4 (IL4) | XM_034870 |
| Homo sapiens interleukin 5 (IL5) | XM_003778 |
| Homo sapiens interleukin 6 (IL6) | XM_033638 |
| Homo sapiens interleukin 7 (IL7) | XM_005266 |
| *Homo sapiens interleukin 8 (IL8)* | *XM_031289* |
| Homo sapiens interleukin 9 (IL9) | XM_003760 |
| Homo sapiens interleukin 10 (IL10) | AY029171 |
| Homo sapiens interleukin 11 (IL11) | XM_035922; XM_008906 |
| Cavia porcellus interleukin-12 p35 subunit (IL12 p35) | AB025723 |
| Homo sapiens interleukin 13 (IL13) | XM_054533; XM_054534 |
| *Homo sapiens interleukin 14 (IL14)* | *XM_034511* |
| Homo sapiens interleukin 15 (IL15) | XM_043810; XM_043811; XM_003529 |
| Homo sapiens granulocyte colony stimulating factor (G-CSF) | NM_000759 |
| Homo sapiens granulocyte macrophage CSF (GM-CSF) | XM_003751; XM_029118 |
| Homo sapiens ciliary neurotrophic factor (CNTF) | XM_006012 |
| Homo sapiens cardiotrophin-1 (CT-1) | XM_008119; NM_001330 |
| Homo sapiens leukemia inhibitory factor (LIF) | XM_038018; XM_009915 |
| Homo sapiens oncostatin M (OSM) | XM_054688; XM_009916 |
| Homo sapiens interferon α (IFNA) | M54886, M38682 |
| Homo sapiens interferon γ (IFNG) | NM_000619 |

- This data was obtained from the National Centre for Biotechnology Information site (URL: http://www.ncbi.nlm.nih.gov/ )

POLYPEPTIDES COMPRISING GROWTH HORMONE RECEPTOR EXTRACELLULAR DOMAIN AND GLYCOSYLPHOSPHATIDYLINOSITOL

This invention relates to polypeptides which comprise a receptor binding domain of a cytokine and a domain which includes a signal sequence for the attachment of glycosylphosphatidylinositol (GPI) anchors; methods to manufacture said polypeptides; nucleic acids molecules encoding said polypeptides; and therapeutic compositions comprising said polypeptides.

GPI-anchors are post-translational modifications to proteins which add glycosyl—phosphatidylinositol which enable these proteins to anchor to extracellular side of cell membranes. Typically proteins which have a GPI anchor do not have transmembrane or a cytoplasmic domain. GPI anchor proteins form a diverse family of proteins that includes by example and not by way of limitation, membrane associated enzymes, adhesion molecules and proteins which coat the outer surface of protozoan parasites such as *Trypanosoma brucei* spp. The kidney includes a number of examples of GPI-anchored proteins ie uromodulin, carbonic anhydrase type IV, alkaline phosphatase, Thy-1, BP-3, amino peptidase P, and dipeptidylpeptidase.

All GPI-anchor proteins are initially synthesized with a transmembrane anchor which, after translocation across the endoplasmic reticulum, is cleaved and covalently linked to a preformed GPI-anchor by a specific transamidase enzyme. The modification of proteins by the addition of a GPI-anchor confers important properties on the protein since the addition of the lipid moiety allows the protein to be inserted into cell membranes thereby anchoring the protein.

There are some general requirements for creating a synthetic GPI anchor sequence. These are a hydrophobic region at the C-terminus of the molecule (10-20 amino acids) not followed by a cluster of basic residues, a "spacer domain" of 7-10 residues preceding the hydrophobic region and small amino acids after the spacer region, where cleavage of the precursor and attachment of the anchor occurs. The GPI anchor is preassembled and added to nascent protein in the endoplasmic reticulum. Concomitant with this step, the initial C-terminal peptide is removed so that the GPI anchor is covalently attached to a new C-terminal amino acid on the protein.

Ligands which interact with receptors to bring about a suitable biochemical response are known as agonists and those that prevent, or hinder, a biochemical response are known as antagonists. For example, and not by way of limitation, cell specific growth factors are ligands that act as agonists and bind receptors located in cell membranes.

A large group of growth factors, referred to as cytokines, are involved in a number of diverse cellular functions. These include, by example and not by way of limitation, modulation of the immune system, regulation of energy metabolism and control of growth and development. Cytokines mediate their effects via receptors expressed at the cell surface on target cells.

Receptors of the cytokine receptor family possess a single transmembrane domain and lack intrinsic enzyme activity (Kishimoto et al., 1994). When a cytokine binds to its cognate receptor the complex is internalised and signaling occurs through the activation of signaling cascades that include the Jak/Stat and Mapk pathways. Internalisation is followed by a recycling step whereby the receptor molecule is regenerated for further use within the cell. An example of the above is described with respect to growth hormone (GH) and its binding to the growth hormone receptor (GHR).

It is known that a single molecule of growth hormone (GH) associates with two receptor molecules (Cunningham et al., 1991; de Vos et al., 1992; Sundstrom et al., 1996; Clackson et al., 1998). This occurs through two unique receptor-binding sites on GH and a common binding pocket on the extracellular domain of two receptors. Site 1 on the GH molecule has a higher affinity than site 2, and receptor dimerization is thought to occur sequentially with one receptor binding to site 1 on GH followed by recruitment of a second receptor to site 2.

The extracellular domain of the GHR exists as two linked domains each of approximately 100 amino acids (SD-100), the C-terminal SD-100 domain being closest to the cell surface and the N-terminal SD-100 domain being furthest away. It is a conformational change in these two domains that occurs on hormone binding with the formation of the trimeric complex GHR-GH-GHR.

Moreover, truncated GH receptors, which lack the cytoplasmic domain of the receptor, act as dominant negative inhibitors of GH signalling (Ross et al., 1997). The truncated receptor is expressed at a high level on the cell surface because it lacks the cytoplasmic domain essential for internalisation (Maamra et al., 1999). In the presence of GH, the truncated receptor heterodimerises with the full length receptor and blocks signalling because it lacks the cytoplasmic domain. As the truncated receptor fails to internalise it acts as a dominant negative inhibitor preventing internalisation of the GH receptor complex.

We have synthesised cytokine receptor variants which comprise a domain of a GPI-anchor protein. The variants lack a cytoplasmic domain and therefore do not have the capability to signal. The provision of a GPI-anchor domain means the variant inserts into membranes and acts as an effective inhibitor of GH signalling by competing for circulating GH and binding GH at the cell surface in a heterodimeric complex that consists of the chimeric truncated GPI anchored receptor, GH, and the native receptor. In addition truncated GPI anchored GH receptor generates a large amount of soluble GH receptor which will bind GH.

Many cytokines activate their cognate receptors via dimerisation or oligomerisation and the invention relates to the provision of cytokine receptors which have been modified by the provision of a polypeptide domain which comprises a sequence which is modified by the addition of glycosylphosphatidylinositol.

According to a first aspect of the invention there is provided a chimeric polypeptide comprising:

i) a ligand binding domain of a cytokine receptor; and ii) a domain which includes a signal sequence for the attachment of glycosylphosphatidylinositol.

Preferably said chimeric polypeptide consists of the extracellular domain of a cytokine receptor and a domain which includes a signal sequence for the attachment of glycosylphosphatidylinositol.

Preferably the polypeptide is modified by the addition of glycosylphosphatidylinositol.

Preferably the modified polypeptide is a modulator of cytokine mediated cell signalling.

Preferably the signal sequence for the attachment of glycosylphosphatidylinositol is selected from the group consisting of:

DKLVKCGGIS LLVQNTSWML LLLLSLSLLQ ALDFISL;  (SEQ ID NO:1)

PSPTPTETAT PSPTPKPTST PEETEAPSSA TTLISPLSLI VIFISFVLLI;  (SEQ ID NO:2)

LVPRGSIEGR GTSITAYNSE GESAEFFFLL ILLLLLVLV;  (SEQ ID NO:3)
and

TSITAYKSE GESAEFFFLL ILLLLLVLV.  (SEQ ID NO:4)

In a preferred embodiment of the invention said polypeptide is an antagonist.

The invention exploits the high affinity of a cytokine for its receptor and the ability of the lipophilic GPI tail to reinsert into a plasma membrane. The polypeptide of the invention is a "chimera" comprising a cytokine receptor ligand binding domain and a domain of a protein which includes a site for the addition of a GPI anchor. The chimeric molecule will consist of the extracellular cytokine hormone binding domain with a C-terminal GPI anchor.

It is expected that in the circulation the chimeric protein will form a micelle of a large number of chimeric proteins with the GPI anchors in the centre. On contact with the cell membrane the GPI will reinsert into the cell membrane. The invention has the important advantage that the binding of the cytokine to the chimera results in a receptor:hormone:chimera complex. In the example of GH this will be GHR:GH:chimera. This complex will not signal as the chimera is a truncated receptor and will therefore block both receptor signaling and internalisation.

In an alternative preferred embodiment of the invention said polypeptide chimera acts as a circulating antagonist. It is expected that the micellar molecule in the circulation will have the GPI anchors at its centre and the binding domain of the receptor pointing outwards and therefore able to bind and antagonise the action of the hormone.

In an alternative preferred embodiment of the invention said polypeptide chimera acts as an antagonist following local or transgenic expression through gene therapy. It would be expected that transfection or gene therapy could be used either at the cellular level or whole body. Thus, the local expression in cells could antagonise the action of cytokines or the injection of DNA into a body compartment such as an inflamed knee would block the actions of inflammatory cytokines such as TNF.

In a preferred embodiment of the invention the ligand binding domain of the cytokine receptor is derived from the receptors selected from the group consisting of: growth hormone (GH); leptin; erythropoietin; prolactin; TNF, interleukins (IL), IL-2, IL-3, IL-4, IL-5, IL-6, IL-7, IL-9, IL-10, IL-11, the p35 subunit of IL-12, IL-13, IL-15; granulocyte colony stimulating factor (G-CSF); granulocyte macrophage colony stimulating factor (GM-CSF); ciliary neurotrophic factor (CNTF); cardiotrophin-1 (CT-1); leukemia inhibitory factor (LIF); oncostatin M (OSM); interferon, IFNα and IFNγ.

Preferably the ligand binding domain of the cytokine receptor is derived from the growth hormone receptor.

In one embodiment of the invention, the polypeptide is a fusion protein.

In a further preferred embodiment of the invention said polypeptide comprises the amino acid sequence shown in FIG. 3 (SEQ ID NO:8) or FIG. 9 (SEQ ID NO:11) or FIG. 14 (SEQ ID NO:14) or FIG. 15 (SEQ ID NO:15).

In a further preferred embodiment of the invention there is provided a polypeptide according to the invention which has been modified by addition, deletion or substitution of at least one amino acid residue to provide a sequence variant of the polypeptide according to the invention.

Typically, variants include chimeras which are modified specifically to alter a feature of the polypeptide unrelated to its physiological activity. For example, cysteine residues can be substituted or deleted to prevent unwanted disulfide linkages. Similarly, certain amino acids can be changed to enhance expression of the chimera by eliminating proteolysis by proteases in an expression system.

Variant chimeras are expressed and tested for one or more activities to determine which mutation provides a variant polypeptide with the desired properties. Further mutations can be made to variants which are silent as to the amino acid sequence of the polypeptide, but which provide preferred codons for translation in a particular host, for example in yeast and slime molds such as *Dictyostelium* spp.

The skilled person will also realize that conservative amino acid substitutions may be made in the chimeric polypeptides to provide functionally equivalent variants of the foregoing polypeptides, i.e, the variants retain the functional capabilities of the chimeras. As used herein, a "conservative amino acid substitution" refers to an amino acid substitution which does not alter the relative charge or size characteristics of the protein in which the amino acid substitution is made.

Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of chimeric polypeptides to produce functionally equivalent variants of these polypeptides typically are made by alteration of a nucleic acid encoding the chimera. Such substitutions can be made by a variety of methods known to one of ordinary skill in the art. For example, amino acid substitutions may be made by PCR-directed mutation, site-directed mutagenesis according to the method of Kunkel, *Proc. Nat. Acad. Sci. U.S.A.* 82: 488-492, 1985.

Alternatively, or preferably, said modification includes the use of modified amino acids in the production of recombinant or synthetic forms of chimeric polypeptides according to the invention.

It will be apparent to one skilled in the art that modified amino acids include, by way of example and not by way of limitation, 4-hydroxyproline, 5-hydroxylysine, $N^6$-acetyllysine, $N^6$-methyllysine, $N^6,N^6$-dimethyllysine, $N^6,N^6,N^6$-trimethyllysine, cyclohexyalanine, D-amino acids, ornithine.

The incorporation of modified amino acids may confer advantageous properties on polypeptides according to the invention. For example, the incorporation of modified amino acids may confer increased in vivo stability on the chimeric polypeptide thus allowing a decrease in the effective amount of polypeptide administered to a patient.

According to a further aspect of the invention there is provided a nucleic acid molecule comprising a nucleic acid sequence which encodes a polypeptide according to the invention.

In a preferred embodiment of the invention said nucleic acid molecule comprises a nucleic acid sequence as represented in FIG. 3 (SEQ ID NO:7) or FIG. 9 (SEQ ID NO:10).

In a preferred embodiment of the invention there is provided a nucleic acid sequence which hybridises under stringent hybridisation conditions to the sequence presented in FIG. 3 (SEQ ID NO:7) or FIG. 9 (SEQ ID NO:10).

According to a further aspect of the invention there is provided a polypeptide encoded by a nucleic acid molecule as represented in FIG. 3 (SEQ ID NO:7) or FIG. 9 (SEQ ID NO:10).

According to a yet further aspect of the invention there is provided a vector including a DNA molecule encoding a polypeptide according to any preceding aspect or embodiment of the invention.

In a preferred embodiment of the invention said vector is an expression vector adapted for eukaryotic gene expression.

Typically said adaptation includes, the provision of transcription control sequences (promoter sequences) which mediate cell/tissue specific expression. These promoter sequences may be cell/tissue specific, inducible or constitutive.

Promoter is an art recognised term and, for the sake of clarity, includes the following features which are provided by example only, and not by way of limitation. Enhancer elements are cis acting nucleic acid sequences often found 5' to the transcription initiation site of a gene (enhancers can also be found 3' to a gene sequence or even located in intronic sequences and are therefore position independent). Enhancers function to increase the rate of transcription of the gene to which the enhancer is linked. Enhancer activity is responsive to trans acting transcription factors (polypeptides) which have been shown to bind specifically to enhancer elements. The binding/activity of transcription factors (please see Eukaryotic Transcription Factors, by David S Latchman, Academic Press Ltd, San Diego) is responsive to a number of environmental cues which include, by example a nd not by way of limitation, intermediary metabolites (eg glucose, lipids), environmental effectors (eg light, heat).

Promoter elements also include so called TATA box and RNA polymerase initiation selection (RIS) sequences which function to select a site of transcription initiation. These sequences also bind polypeptides which function, inter alia, to facilitate transcription initiation selection by RNA polymerase.

Adaptations also include the provision of selectable markers and autonomous replication sequences which both facilitate the maintenance of said vector in either the eukaryotic cell. Vectors which are maintained autonomously are referred to as episomal vectors.

Adaptations which facilitate the expression of vector encoded genes include the provision of transcription termination/polyadenylation sequences. This also includes the provision of internal ribosome entry sites (IRES) which function to maximise expression of vector encoded genes arranged in bicistronic or multi-cistronic expression cassettes.

These adaptations are well known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994).

It will be apparent to one skilled in the art that the vectors according to the invention could be gene therapy vectors. Gene therapy vectors are typically viral based. A number of viruses are commonly used as vectors for the delivery of exogenous genes. Commonly employed vectors include recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. Chimeric vectors may also be employed which exploit advantageous elements of each of the parent vector properties (See e.g., Feng, et al. (1997) Nature Biotechnology 15:866-870). Such viral vectors may be wild-type or may be modified by recombinant DNA techniques to be replication deficient, conditionally replicating or replication competent.

Preferred vectors are derived from the adenoviral, adeno-associated viral and retroviral genomes. In the most preferred practice of the invention, the vectors are derived from the human adenovirus genome. Particularly preferred vectors are derived from the human adenovirus serotypes 2 or 5. The replicative capacity of such vectors may be attenuated (to the point of being considered "replication deficient") by modifications or deletions in the E1a and/or E1b coding regions. Other modifications to the viral genome to achieve particular expression characteristics or permit repeat administration or lower immune response are preferred.

Alternatively, the viral vectors may be conditionally replicating or replication competent. Conditionally replicating viral vectors are used to achieve selective expression in particular cell types while avoiding untoward broad spectrum infection. Examples of conditionally replicating vectors are described in Pennisi, E. (1996) Science 274:342-343; Russell, and S. J. (1994) Eur. J. of Cancer 30A(8):1165-1171. Additional examples of selectively replicating vectors include those vectors wherein an gene essential for replication of the virus is under control of a promoter which is active only in a particular cell type or cell state such that in the absence of expression of such gene, the virus will not replicate. Examples of such vectors are described in Henderson, et al., U.S. Pat. No. 5,698,443 issued Dec. 16, 1997 and Henderson, et al., U.S. Pat. No. 5,871,726 issued Feb. 16, 1999 the entire teachings of which are herein incorporated by reference.

Additionally, the viral genome may be modified to include inducible promoters which achieve replication or expression only under certain conditions. Examples of inducible promoters are known in the scientific literature (See, e.g. Yoshida and Hamada (1997) Biochem. Biophys. Res. Comm. 230:426-430; lida, et al. (1996) J. Virol. 70(9):6054-6059; Hwang, et al. (1997) J. Virol 71(9):7128-7131; Lee, et al. (1997) Mol. Cell. Biol. 17(9):5097-5105; and Dreher, et al. (1997) J. Biol. Chem 272(46); 29364-29371.

Vectors may also be non-viral and are available from a number of commercial sources readily available to the man-skilled in the art. For example the vectors may be plasmids which can be episomal or integrating.

In a further aspect of the invention there is provided a method to prepare a polypeptide according to the invention comprising:

(i) growing a cell transfected with a vector or nucleic acid of the present invention in conditions conducive to the manufacture of said polypeptide; and (ii) purifying said polypeptide from said cell, or its growth environment.

In a preferred method of the invention said vector encodes, and thus said recombinant polypeptide is provided with, a secretion signal to facilitate purification of said polypeptide.

In yet a further embodiment of the invention there is provided a cell transfected with the vector or nucleic acid according to the invention.

Preferably said eukaryotic cell is selected from the group consisting of: a fungal cell eg *Saccharomyces cerevisiae, Pichia* spp; slime mold (eg *Dictyostelium* spp); insect (eg *Spodoptera frugiperda*); a plant cell; or a mammalian cell.

In a further preferred embodiment of the invention said eukaryotic cell is *Dictyostelium* spp.

According to a further aspect of the invention there is provided the use of the polypeptide according to the invention as a pharmaceutical. Preferably said polypeptide is used in a pharmaceutical composition.

When administered the polypeptide of the present invention is administered in pharmaceutically acceptable preparations. Such preparations may routinely contain pharmaceutically acceptable concentrations of salt, buffering agents, preservatives, compatible carriers, and optionally other therapeutic agents.

The polypeptide of the invention can be administered by any conventional route, including injection. The administration may, for example, be oral, intravenous, intraperitoneal, intramuscular, intracavity, subcutaneous, or transdermal.

Pharmaceutical compositions of the invention are administered in effective amounts. An "effective amount" is that amount of a composition that alone, or together with further doses, produces the desired response. This may involve only slowing the progression of the disease temporarily, although more preferably, it involves halting the progression of the disease permanently. This can be monitored by routine methods or can be monitored according to diagnostic methods.

The doses of the polypeptide administered to a subject can be chosen in accordance with different parameters, in particular in accordance with the mode of administration used and the state of the subject (ie age, sex). When administered, the pharmaceutical compositions of the invention are applied in pharmaceutically-acceptable amounts and in pharmaceutically-acceptable compositions. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The pharmaceutical compositions may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous or non-aqueous preparation which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

According to a further aspect of the invention there is provided the use of the polypeptide according to the invention for the manufacture of a medicament for use in the treatment of a disease selected from the group consisting of: acromegaly; gigantism; diabetes mellitus; cancer; anorexia; autoimmune and infectious disease; inflammatory disorders including rheumatoid arthritis.

In a preferred embodiment of the invention said disease is acromegaly.

In a further preferred embodiment of the invention said disease is gigantism.

In a yet further preferred embodiment of the invention said disease is cancer.

The invention also provides for a method of treating a human or animal subject comprising administering an effective amount of the polypeptide pharmaceutical composition or medicament to said subject.

The invention also provides a method of reduced renal clearance of a molecule comprising forming an agent according to any embodiment of the invention. The size of the micelles reduce renal clearance.

An embodiment of the invention will now be described by example only and with reference to the following figures wherein;

FIG. 1 shows the nucleotide sequence (SEQ ID NO:5) of vector pAc6-LP-MCS-GPI used to clone the extracellular domain of the GHR for expression in Dictyostelium;

FIG. 2 shows part of the multiple cloning site (SEQ ID NO:6) of pAc6-LP-MCS-GPI with the extracellular domain of the GHR cloned in and the new vector is called pAc6GHRGPI. The extracellular domain of the GHR is in capitals;

FIG. 3 represents the GHRGPI fusion nucleic acid (SEQ ID NO:7) and amino acid (SEQ ID NO:8) sequence from vector pAc6GHRGPI. The nucleotide for the extracellular domain of the GHR is in capitals and the amino acid sequence is in bold;

Figure 4:
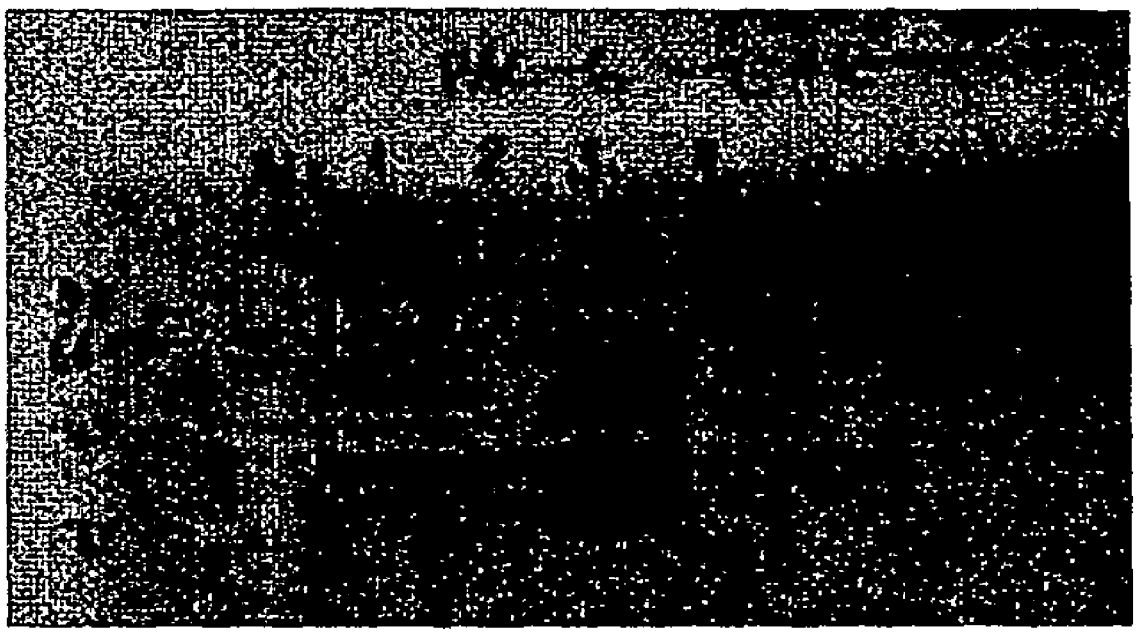
Figure 5:
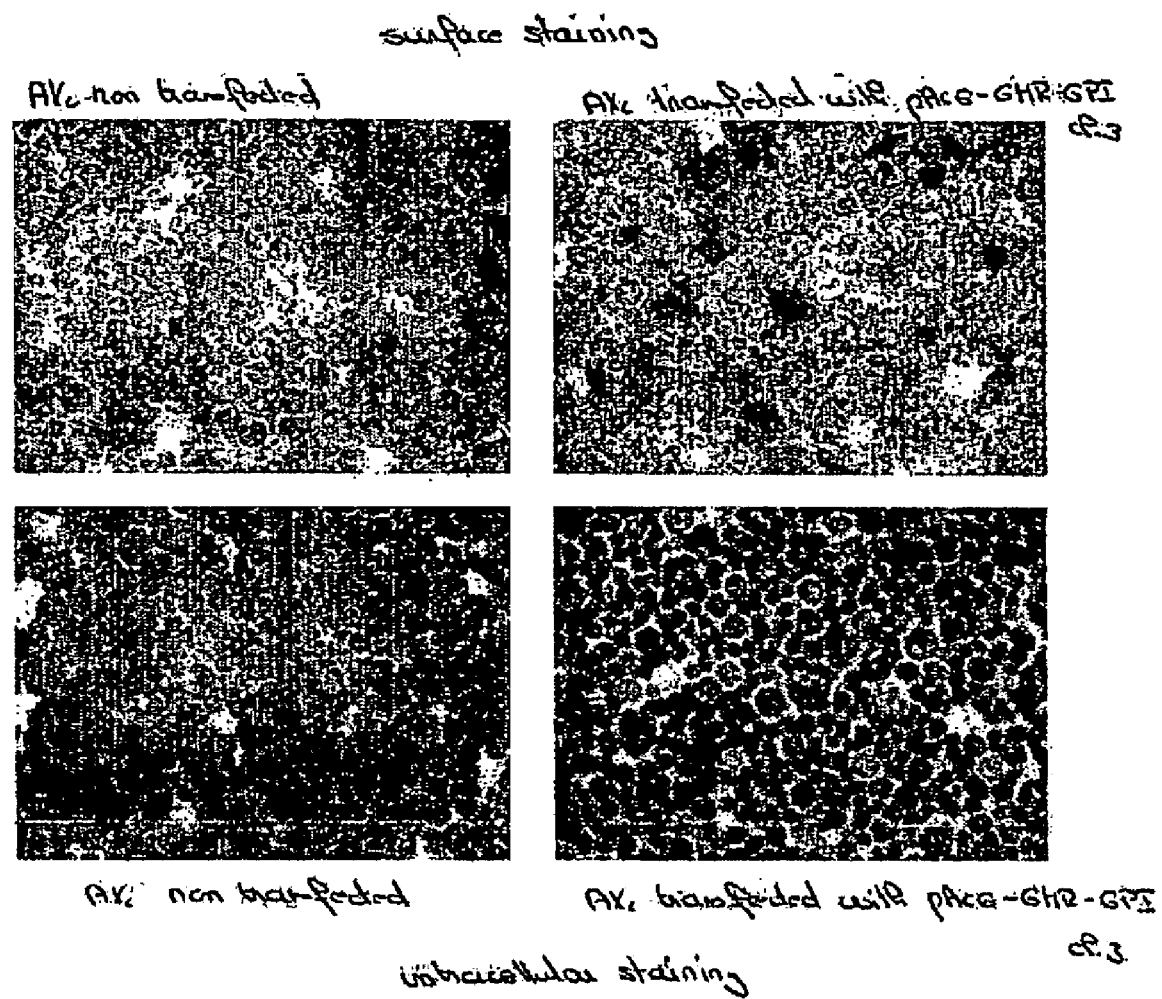
Figure 6:
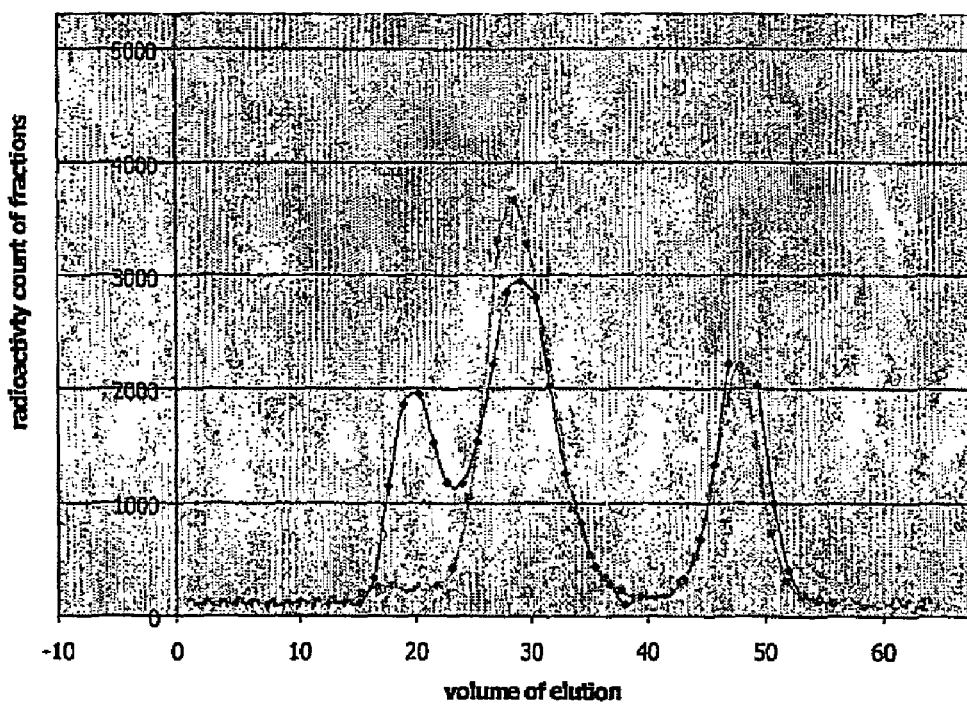
Figure 7:
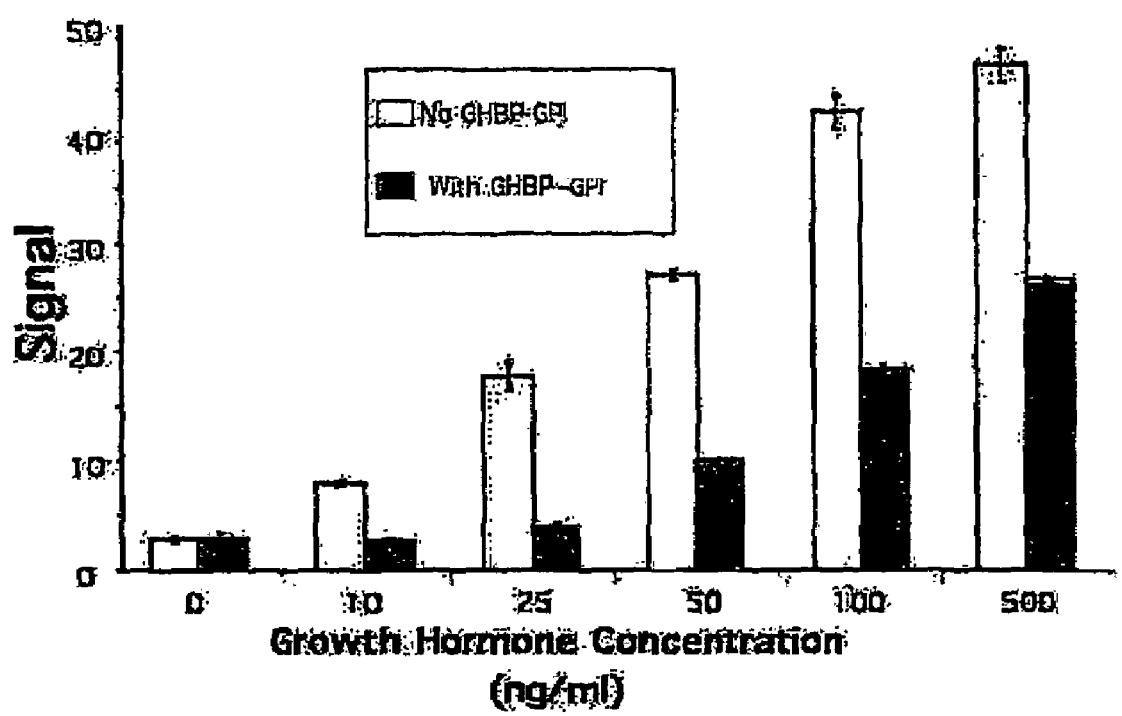
Figure 10:
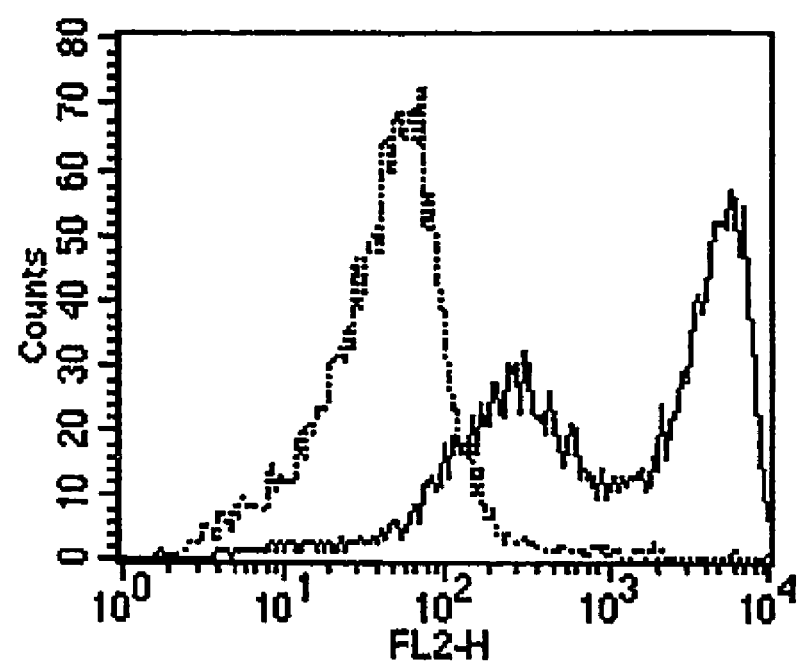
Figure 11:
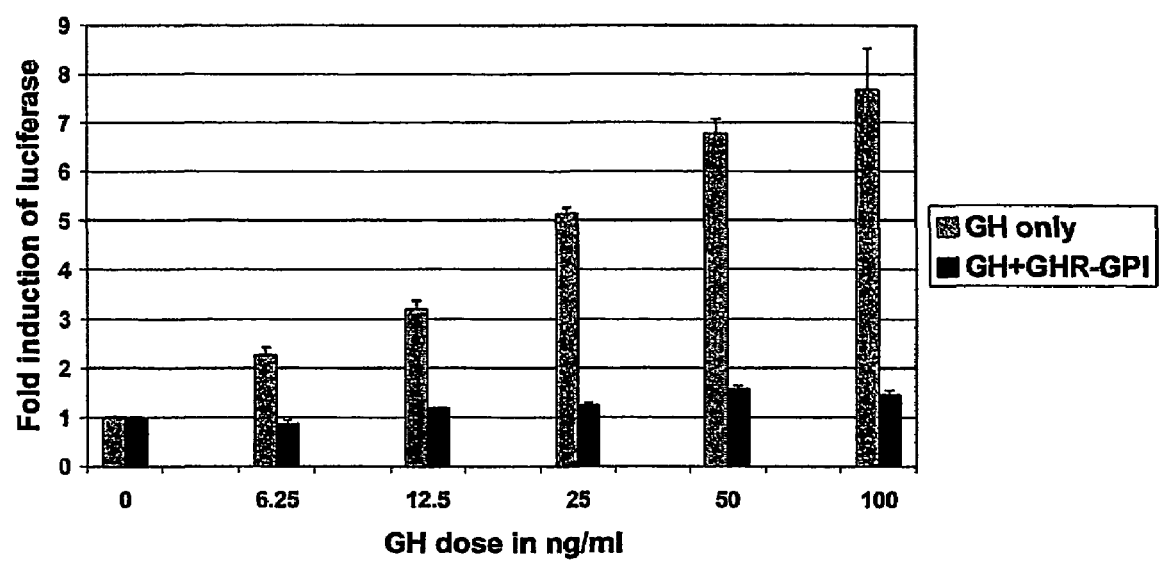

FIG. 4 illustrates screening for GHRGPI in cell lysates from Dictyostelium clones transfected with pAc6GHRGPI. Screening was performed by western blotting using a monoclonal antibody to the GHR, Mab5. Lane A X2 is a negative control of untransfected cells and lanes 1-7 different screened clones. Lanes 1, 2, 3, & 5 show a positive band at the correct size and lane 3 was selected for purification of GHRGPI;

FIG. 5 illustrates immunostaining for GHRGPI and demonstrates that the protein is expressed at the Dictyostelium cell surface. The upper panels show surface staining with a negative control on the left of untransfected cells, on the right the cells transfected with pAc6GHRGPI show positive immunostaining on the cell surface. In the lower panels the cells have been permeabilised to study intracellular staining. Again the negative control is on the left and the positive control on the right shows intracellular staining;

FIG. 6 Elution profile (Sephadex G100) of iodinated GH alone, and GHRGPI (purified from stable Dictyostelium clones expressing the GHRGPI identified in FIG. 5) with iodinated GH plus or minus cold GH. GHR-GPI forms single complex of around 60-65 Kda with 125 I-GH (blue line). The yellow line is iodinated GH alone and the pink line GHR-GPI in the presence of excess cold GH. The result shows functional binding of GH by purified GHRGPI;

FIG. 7 shows a bioassay for growth hormone in the presence or absence of purified GHRGPI. Cells expressing the growth hormone receptor are transfected with a luciferase reporter activated by growth hormone signalling. The cells were then stimulated with increasing doses of growth hormone in the presence or absence of GHRGPI (approximately 10 nM). In the presence of GHRGPI the growth hormone signal was abolished at low doses of growth hormone or reduced a high doses;

FIG. 8 is pCR-3GPI_Thy-1 a mammalian expression vector with mammalian GPI signal (SEQ ID NO:9);

FIG. 9 is the nucleotide (SEQ ID NO:10) and amino acid (SEQ ID NO:11) sequence of a mammalian GHRGPI anchor polypeptide in pCR-3GPI_Thy-1 and called pCR3GHRGPI. The extracellular domain of the GHR is ligated into the BamHI and EcorI site. For the amino acid sequence bold is extracellular domain GHR, bold italics underlined is GHR signal and underlined is start of the GPI signal which is cleaved;

FIG. 10 FACS analysis of CHO cells transfected with vector only (thin line) and with pCR3GHRGPI thick line immunostained with GHR specific monoclonal antibody and demonstrating that almost all CHO cells are expressing a high level of GHRGPI;

FIG. 11 GH activation of Stat5 (fold induction of luciferase) in HEK293 cells expressing the GH receptor (GH only) and cells transfected with GHRGPI plasmid. Demonstrates that transgenic expression of GHRGPI (extracellular domain GHR linked to GPI) completely inhibits GH signalling;

FIG. 12 Measurement of soluble GH receptor (GHBP) in media from mammalian cells undoing going transfection with various vectors. The results were obtained by the GHBP-LIFA (ligand immunofunctional assay) and "<70" means below the lowest standard of the assay. The results demonstrate that expression of GHRGPI in cells results in very high levels of soluble receptor in the medium;

FIG. 13 represents the amino acid and nucleotide sequence (SEQ ID NO:13) of TNF receptor type 1. Protein sequence P19438, signal in green and transmembrane helix in red. Nucleic acid sequence X55313 *H. sapiens* TNF-R m . . . [gi:37223]. 256-318 is signal and 319-888 extracellular domains;

FIG. 14 represents the amino acid sequence (SEQ ID NO:14) of a TNF receptor type 1-GPI fusion polypeptide from vector pCR3TNFGPI after cloning of extracellular domain TNF receptor into the vector pCR-3GPI_Thy-1 (FIG. 8). Bold is extracellular domain TNF receptor, bold italics underlined is TNF receptor signal and underlined is start of the GPI signal which is cleaved;

FIG. 15 represents the amino acid sequence (SEQ ID NO:15) of the leptin receptor-GPI fusion from pCR3ObRGPI after cloning of extracellular domain leptin receptor (ObR) into the vector pCR-3GPI_Thy-1 (FIG. 8). Italics ObR signal, bold ObR extracellular domain, then the link to GPI then underlined the cleavage site for GPI FIG. 16 is a table of cytokine accession numbers.

MATERIALS AND METHODS

Purification of Extracellular Domain Cytokine
Receptor Fusion with GPI from Dictyostelium and
Demonstration of Antagonist Activity Transfection and Maintenance of Dictylostelium Strains Dictylostelium were transfected by the calcium phosphate method or electroporation and maintained in culture medium with G418 to select stable clones.

Cloning and Expression of Chimeric Polypeptides

The cDNA extracellular domain of the human GHR (bases 98-834, accession number X06562) was ligated into a vector (pAc6-LP-MCS-GPI) containing the *Dictyostelium* actin 6 gene promoter, a *Dictyostelium* signal peptide coding region, multiple cloning site and the signal (PSPTPTETAT PSPTPKPTST PEETEAPSSA TTLISPLSLI VIFISFVLLI) (SEQ ID NO:2) for a GPI anchor. The resultant vector (pAc6-GHR-GPI) was transfected into *Dictyostelium* cells.

*Dictyostelium* adds N and O-glycosylations. Clones expressing GHR-GPI were then selected by immunohistochemistry and western blotting using an anti-GHR antibody Mab5. GHR-GPI was purified from cell lysates using a GH affinity column. Purified GHR-GPI was demonstrated to bind GH and in a bioassay for GH signalling GHR-GPI acted as an antagonist inhibiting signalling.

The vector pAc6-LP-MCS-GPI (FIG. 1) was digested with BamHI and EcORI. Extracellular domain GHR from base 98-834 (accession X06562) was amplified by PCR with BamHI and EcORI restriction sites 5' and 3' respectively and then ligated into the MCS of pAc6-LP-MCS-GPI to give the following MCS: cag gat cca ttt . . . GHR 98-834 . . . tac cga att cca (FIG. 2) (SEQ ID NO:6). The encoded GHR protein is from the first residue after the mammalian signal peptide to the last residue before the transmembrane domain. The resultant vector was called pAc6-GHR-GPI.

Purification of GHR-GPI

The cDNA for pAc6-GHR-GPI was transfected into *Dictyostelium* cells and clones were then selected and screened by western blotting using Mab5, a monoclonal antibody to the extracellular domain of the human GHR. Five clones gave a clear signal at 40kDa, the expected size of glycosylated GHR-GPI (FIG. 4). Immunostaining of one clone clearly identified GHR-GPI on the cell surface (FIG. 5). Cell lysate in 0.1% Triton X100 were then purified on a GH affinity column in PBS/0.1% Triton X 100 (Na-phosphate 0.01 M, NaCl 0.15M, 0.02% NaNO3, 0.1% Triton X-100 Ph 7.4). The approximate concentration of GHR-GPI was 120 ug/ml or 3 µM. Functional activity of the purified GHRGPI was confirmed by binding of iodinated GH (FIG. 6).

GH Bioassay

An established bioassay was used to screen for antagonist activity (Ross et al., 1997). A permanent cell line expressing the full length GHR was transiently transfected with a luciferase reporter that binds activated Stat5. Twenty-four hours later the cells are stimulated with GH for 6 hours with or without antagonist. The cells are then lysed and luciferase activity measured. The bioassay was performed in the presence or absence of GHR-GPI at a concentration of approximately 10 nM (FIG. 7). The GHR-GPI completely blocked signalling at low concentration of GH and caused an approximate 50% reduction in signalling at higher concentrations of GH confirming the antagonistic action of GHR-GPI on GH signalling.

Cloning of Extracellular Domain Cytokine Receptor GPI Fusion into Mammalian Expression Vector and Demonstration of Antagonist Activity when Expressed in Cytokine Responsive Cell Line GHR-GPI can act as a transgenic therapy.

To demonstrate that GHR-GPI can act as a transgenic therapy we have cloned the extracellular domain of the GHR upstream of a mouse GPI signal sequence in a mammalian expression vector (FIGS. 8-9). This construct was then transfected into CHO cells and expression demonstrated by FACS analysis using a monoclonal antibody specific for the human GHR (FIG. 10). The level of binding on CHO cells was extremely high. To test whether the GHR-GPI expression on the cell surface was acting as antagonist the GHR-GPI was transfected into the Hek293 cells expressing the wild-type GHR and stimulated with GH. This co-expression of GHR-GPI completely blocked GH signaling (FIG. 11). In addition the media from cells transfected with GHR-GPI was measured for soluble receptor (GHBP) and high levels were found (FIG. 12) providing another mechanism by which the transgenic expression of cytokine GPI fusions could act as antagonists. Other examples of cytokine receptors that could be expressed as GPI fusions are the TNF and leptin receptors (FIGS. 13-16).

REFERENCES

ARGETSINGER, L. S. & CARTER-SU, C. (1996) Growth hormone signalling mechanisms: involvement of the tyrosine kinase JAK2. [Review] [19 refs]. *Hormone Research*, 45 Suppl 1, 22-24.

CHEN, C., BRINKWORTH, R. & WATERS, M. J. (1997) The role of receptor dimerization domain residues in growth hormone signaling. *Journal of Biological Chemistry*, 272, 5133-5140.

CHEN, W. Y., CHEN, N. Y., YUN, J., WAGNER, T. E. & KOPCHICK, J. J. (1994) In vitro and in vivo studies of antagonistic effects of human growth hormone analogs [published erratum appears in J Biol Chem 1994 Aug. 12;269(32):20806]. *Journal of Biological Chemistry*, 269, 15892-15897.

CHEN, W. Y., WHITE, M. E., WAGNER, T. E. & KOPCHICK, J. J. (1991) Functional antagonism between endogenous mouse growth hormone (GH) and a GH analog results in dwarf transgenic mice. *Endocrinology*, 129, 1402-1408.

CHEN, W. Y., WIGHT, D. C., MEHTA, B. V., WAGNER, T. E. & KOPCHICK, J. J. (1991) Glycine 119 of bovine growth hormone is critical for growth-promoting activity. *Molecular Endocrinology*, 5, 1845-1852.

CHEN, W. Y., WIGHT, D. C., WAGNER, T. E. & KOPCHICK, J. J. (1990) Expression of a mutated bovine growth hormone gene suppresses growth of transgenic mice. *Proceedings of the National Academy of Sciences of the United States of America*, 87, 5061-5065.

CLACKSON, T., ULTSCH, M. H., WELLS, J. A. & DEVOS, A. M. (1998) Structural and functional analysis of the 1:1 growth hormone:receptor complex reveals the molecular basis for receptor affinity. *Journal of Molecular Biology*, 277, 1111-1128.

CUNNINGHAM, B. C., ULTSCH, M., DE VOS, A. M., MULKERRIN, M. G., CLAUSER, K. R. & WELLS, J. A. (1991) Dimerization of the extracellular domain of the human growth hormone receptor by a single hormone molecule. *Science*, 254, 821-825.

DA COSTA, C. R. & JOHNSTONE, A. P. (1998) Production of the thyrotrophin receptor extracellular domain as a glycosylphosphatidylinositol-anchored membrane protein and its interaction with thyrotrophin and autoantibodies. *Journal of Biological Chemistry*, 273, 11874-11880.

DE VOS, A. M., ULTSCH, M. & KOSSIAKOFF, A. A. (1992) Human growth hormone and extracellular domain of its receptor: crystal structure of the complex. *Science*, 255, 306-312.

FUH, G., CUNNINGHAM, B. C., FUKUNAGA, R., NAGATA, S., GOEDDEL, D. V. & WELLS, J. A. (1992) Rational design of potent antagonists to the human growth hormone receptor. *Science*, 256, 1677-1680.

KISHIMOTO, T., TAGA, T. & AKIRA, S. (1994) Cytokine signal transduction. [Review] [92 refs]. *Cell*, 76, 253-262.

MAAMRA, M., FINIDORI, J., VON LAUE, S., SIMON, S., JUSTICE, S., WEBSTER, J., DOWER & ROSS, R. (1999) Studies with a growth hormone antagonist and dual-fluorescent confocal microscopy demonstrate that the full-length human growth hormone receptor, but not the truncated isoform, is very rapidly internalized independent of Jak2-Stat5 signaling. *Journal of Biological Chemistry*, 274, 14791-14798.

MELLADO, M., RODRIGUEZ-FRADE, J. M., KREMER, L., VON KOBBE, C., DE ANA, A. M., MERIDA, I. & MARTINEZ, A. (1997) Conformational changes required in the human growth hormone receptor for growth hormone signaling. *Journal of Biological Chemistry*, 272, 9189-9196.

MULLER-NEWEN, G., KOHNE, C. & HEINRICH, P. C. (1996) Soluble receptors for cytokines and growth factors. [Review] [58 refs]. *International Archives of Allergy & Immunology,* 111, 99-106.

ROSS, R. J., ESPOSITO, N., SHEN, X. Y., VON LAUE, S., CHEW, S. L., DOBSON, P. R., POSTEL-VINAY, M. C. & FINIDORI, J. (1997) A short isoform of the human growth hormone receptor functions as a dominant negative inhibitor of the full-length receptor and generates large amounts of binding protein. *Molecular Endocrinology,* 11, 265-273.

ROSS, R. J. M., LEUNG, K. C., MAAMRA, M., BENNETT, W., DOYLE, n., WATERS, M. J. & HO, k.k.y. (2000) Binding and functional studies with the growth hormone receptor antagonist, B2036-PEG (pegvisomant), reveal effects of pegylation. *Journal of Clinical Endocrinology & Metabolism,* In press SUNDSTROM, M., LUNDQVIST, T., RODIN, J., GIEBEL, L. B., MILLIGAN, D. & NORSTEDT, G. (1996) Crystal structure of an antagonist mutant of human growth hormone, G120R, in complex with its receptor at 2.9 A resolution. *Journal of Biological Chemistry,* 271, 32197-32203.

THORNER, M. O., STRASBURGER, C. J., WU, Z., STRAUME, M., BIDLINGMAIER, M., PEZZOLI, S., ZIB, K., SCARLETT, J. C. & BENNETT, W. F. (1999) Growth hormone (GH) receptor blockade with a PEG-modified GH (B2036-PEG) lowers serum insulin-like growth factor-I but does not acutely stimulate serum GH. *Journal of Clinical Endocrinology & Metabolism,* 84, 2098-2103.

The invention claimed is:

1. An isolated nucleic acid molecule which encodes a chimeric polypeptide comprising:
   (i) an extracellular cytokine binding domain of human growth hormone receptor; and
   (ii) a domain which includes a signal sequence for attachment of glycosylphosphatidylinositol,
wherein said nucleic acid molecule comprises the nucleic acid sequence set forth in SEQ ID NO: 7.

2. A vector comprising the nucleic acid molecule according to claim 1.

3. A vector according to claim 2, wherein said vector is an expression vector adapted for eukaryotic gene expression.

4. A vector according to claim 3, wherein said vector encodes a recombinant polypeptide comprising a secretion signal for facilitating purification of said polypeptide.

5. A method of preparing a polypeptide, said method comprising:
   (i) growing a cell transfected with a nucleic acid according to claim 1, or a vector comprising a nucleic acid according to claim 1 in an in vitro growth environment under conditions conducive to the manufacture of said polypeptide; and
   (ii) purifying said polypeptide from said cell or said growth environment.

6. An isolated eukaryotic cell transfected with a nucleic acid according to claim 1 or a vector comprising a nucleic acid according to claim 1.

7. A eukaryotic cell according to claim 6, wherein said cell is selected from the group consisting of a fungal cell, a slime mold cell, an insect cell, a plant cell and a mammalian cell.

8. A cell according to claim 7, wherein said cell is a slime mold cell and is *Dictyostelium* spp.

9. A polypeptide encoded by a nucleic acid molecule of claim 1, wherein the polypeptide comprises SEQ ID NO: 8.

10. A micelle comprising a plurality of polypeptides according to claim 1.

* * * * *

SEQUENCE LISTING

```
<160> NUMBER OF SEQ ID NOS: 15

<210> SEQ ID NO 1
<211> LENGTH: 37
<212> TYPE: PRT
<213> ORGANISM: artificial sequence
<220> FEATURE:
<221> NAME/KEY: signal
<223> OTHER INFORMATION: signal sequence for the attachment of
      glycophosphatidylinositol

<400> SEQUENCE: 1

Asp Lys Leu Val Lys Cys Gly Gly Ile Ser Leu Leu Val Gln Asn Thr
1               5                   10                  15

Ser Trp Met Leu Leu Leu Leu Ser Leu Ser Leu Leu Gln Ala Leu
            20                  25                  30

Asp Phe Ile Ser Leu
            35

<210> SEQ ID NO 2
<211> LENGTH: 50
<212> TYPE: PRT
<213> ORGANISM: artificial sequence
<220> FEATURE:
<221> NAME/KEY: signal
<223> OTHER INFORMATION: signal sequence for the attachment of
      glycophosphatidylinositol

<400> SEQUENCE: 2

Pro Ser Pro Thr Pro Thr Glu Thr Ala Thr Pro Ser Pro Thr Pro Lys
1               5                   10                  15

Pro Thr Ser Thr Pro Glu Glu Thr Glu Ala Pro Ser Ser Ala Thr Thr
            20                  25                  30

Leu Ile Ser Pro Leu Ser Leu Ile Val Ile Phe Ile Ser Phe Val Leu
            35                  40                  45

Leu Ile
    50

<210> SEQ ID NO 3
<211> LENGTH: 39
<212> TYPE: PRT
<213> ORGANISM: artificial sequence
<220> FEATURE:
<221> NAME/KEY: signal
<223> OTHER INFORMATION: signal sequence for the attachment of
      glycophosphatidylinositol
```

```
<400> SEQUENCE: 3

Leu Val Pro Arg Gly Ser Ile Glu Gly Arg Gly Thr Ser Ile Thr Ala
1               5                   10                  15

Tyr Asn Ser Glu Gly Glu Ser Ala Glu Phe Phe Phe Leu Leu Ile Leu
                20                  25                  30

Leu Leu Leu Leu Val Leu Val
            35

<210> SEQ ID NO 4
<211> LENGTH: 28
<212> TYPE: PRT
<213> ORGANISM: artificial sequence
<220> FEATURE:
<221> NAME/KEY: signal
<223> OTHER INFORMATION: signal sequence for the attachment of
      glycophosphatidylinositol

<400> SEQUENCE: 4

Thr Ser Ile Thr Ala Tyr Lys Ser Glu Gly Glu Ser Ala Glu Phe Phe
1               5                   10                  15

Phe Leu Leu Ile Leu Leu Leu Leu Leu Val Leu Val
                20                  25

<210> SEQ ID NO 5
<211> LENGTH: 6283
<212> TYPE: DNA
<213> ORGANISM: artificial sequence
<220> FEATURE:
<223> OTHER INFORMATION: vector used to clone extracellular domain of
      GHR pAc6-LP-MCS-GPI
<220> FEATURE:
<221> NAME/KEY: misc_feature
<222> LOCATION: (301)..(306)
<223> OTHER INFORMATION: Unknown nucleotide

<400> SEQUENCE: 5
caactcagtc ccacgtttcg cgcgtttcgg tgatgacggt gaaaacctct gacacatgca      60
gctcccggag acggtcacag cttgtctgta agcggatgcc gggagcagac aagcccgtca     120
gggcgcgtca gcgggtgttg gcgggtgtcg gggctggctt aactatgcgg catcagagca     180
gattgtactg agagtgcacc ataatccttt tcatggagat tgtattatat gtgagaatcg     240
tttacccata aagggtaaaa ttattaattt tttttttttt tcaaatttta acgttaaagc     300
nnnnnngcaa ataccttaat atctggattt ttaattttt ttgtaattta aaaaatgata     360
attaaagtaa taataaaaaa taaaaaaaca attaaaaaaa aaaccaatag cctattggtt     420 ttatttttt ttttttaagg tcggataaag atcaacaacc attaaaaaaa aagtaattaa      480 atttattat acatttaaat attattattg ttatattatt attattattt ttatgtgaag     540
cactttcatc atgatttaga acatttttct gtggacaatt gatggaccag attcatcata     600
ttcttctttt gagatccaca tttgttggaa agttgagagt gaagctaaaa tagatccacc     660
aatccagaca gagtatttac gttctggtgg agcaatgatt ttaatttca tggttgatgg     720 tgctaaagca gttaattctt tgttcatacg atcagcaata cctgggaaca tagttgtacc     780
acctgataag acgacattac cgtataaatc tttacggatg atccctgtaa tccgggcagc     840
gcaacggaac attcatcagt gtaaaaatgg aatcaataaa gccctgcgca gcgcgcaggg     900
tcagcctgaa tacgcgttta atgaccagca cagtcgtgat ggcaaggtca gaatagcgct     960
gaggtctgcc tcgtgaagaa ggtgttgctg actcatacca ggcctgaatc gccccatcat    1020
```

```
ccagccagaa agtgagggag ccacggttga tgagagcttt gttgtaggtg gaccagttgg    1080
tgattttgaa cttttgcttt gccacggaac ggtctgcgtt gtcgggaaga tgcgtgatct    1140
gatccttcaa ctcagcaaaa gttcgattta ttcaacaaag ccgccgtccc gtcaagtcag    1200
cgtaatgctc tgccagtgtt acaaccaatt aaccaattct gattagaaaa actcatcgag    1260
catcaaatga aactgcaatt tattcatatc aggattatca ataccatatt tttgaaaaag    1320
ccgtttctgt aatgaaggag aaaactcacc gaggcagttc cataggatgg caagatcctg    1380
gtatcggtct gcgattccga ctcgtccaac atcaatacaa cctattaatt tccctcgtc     1440 aaaaataagg ttatcaagtg agaaatcacc atgagtgacg actgaatccg gtgagaatgg    1500
caaaagctta tgcatttctt tccagacttg ttcaacaggc cagccattac gctcgtcatc    1560
aaaatcactc gcatcaacca aaccgttatt cattcgtgat tgcgcctgag cgagacgaaa    1620
tacgcgatcg ctgttaaaag gacaattaca acaggaatc gaatgcaacc ggcgcaggaa     1680
cactgccagc gcatcaacaa tattttcacc tgaatcagga tattcttcta atacctggaa    1740
tgctgttttc ccggggatcg cagtggtgag taaccatgca tcatcaggag tacggataaa    1800
atgcttgatg gtcggaagag gcataaattc cgtcagccag tttagtctga ccatctcatc    1860
tgtaacatca ttggcaacgc tacctttgcc atgtttcaga acaactctg gcgcatcggg      1920 cttcccatac aatcgataga ttgtcgcacc tgattgcccg acattatcgc gagcccattt    1980
atacccatat aaatcagcat ccatgttgga atttaatcgc ggccttgttt taagaaataa    2040 gaaaaaaaa aaaaaaaaat ctttttatgc aatctgaaaa aaaaaaaaaa aaaaaaaaaa      2100 aaaaaaaaa aaaaaaaaaa aattttttgaa tcccattttt tttttttaat ttgggtttta    2160
aaattttcaa ataataatta accaacccaa gttttttttaa accattttttt ttttttaaaga  2220 tttgatggga ttaattaatt tgtaatctat ttaattcaaa ataaataaaa ataaataaaa    2280
atttttttta tcgatctcga gactagagag gtttattttt aaaaattaca aaaactaaaa    2340
agaaaaataa aaaggaaaaa tcttattaat ctgaaaatta cagatttgcc ccaatttaaa    2400
gaaaaattat ccaaaataat caatcaacaa cgatatcttt ttgatagata tttataaaaa    2460
ctttatcttt tttatttttt caagttgcgc aaaataataa aattaaaata aatataaaaa    2520
ctgtaaaaag aaaaaaaaaa gtgtaaaggt ttattaatta tttaattatt attcactttt    2580
tgtaattatt tttttatttt gaagaataat gatggatatt ttatataaaa aaaaaaagag    2640
atactgaaaa aataataatt ataaaaaaaa aaaaaaaaaa tagaatttta aagttttagt    2700
acaaatggat gatttttttt tttttttttt tttttccca ataattcaa gtaataacaa      2760 caaagaacgg atattctgat gcctaattaa aaaagaaatt tttaaataaa aaatgggttt    2820
tttttaagta aagttatttg aaattgattg aaattttcaa accatgggtg gttttcgct     2880 ttaaaattgg gattttattt ttattttttt atattttta ttttttattt tttttttttt     2940
gaggtttctg agattataaa atgaaatttt ttttctgat gcctaattaa aaagaaatt      3000 tttaaataaa aaatggcttt tttttaagta aagttatttg aaatcgattg aaattttcaa    3060
accatgggtg gttttcgct ttaaaattgg gattttattt ttattttttt atattttta      3120 tttttatttt tttttttttt gaggtttctg agattataaa atgaaatttt tttttttttt    3180
ttaattaatt caaaaaaata atcaaataaa taaatataat ataaaatgtc tagattttta    3240
ttagtattga taatattata taatatttta aatagtgcac attcagctcc aacccaggat    3300
ccaggtacca tggttaacgg agctcgaatt ccatctccaa ctccaactga acagccacc     3360 ccatctccaa ctccaaaacc aaccagcaca ccagaagaaa ctgaagcacc ttcatcagca    3420
```

```
acaactctta tttcaccatt atctttaatt gttattttca tttctttgt tttattaatt    3480 taagagctcg ctagagtcgt ccatcaattg ttcacagaaa atgtttctaa attatttaat    3540
aaataataaa aaaacaaatt gttgtaataa tctaatattt tctttttttt ttaatttttt    3600
ttttttaaat cttaataatt attaagttat tttaatttt tttttttttt tttttttttt    3660
tttttttttt ttctatcaaa aaatcaaat atatttaaaa aatttattat ttacagtaca    3720
ttttgaatgg tgaagataaa tatatgcatt agatgtaaaa ggcgactggt cgtccatcaa    3780
ttgttcacag aaaatgtttc taaattattt aataaataat aaaaaaacaa attgttgtaa    3840
taatctaata ttttctttt tttttaattt tttttttta aatcttaata attattaagt    3900
tattttaatt tttttttttt tttttttttt tttttttttt tttttctatc aaaaaaatca    3960
aatatattta aaaatttat tatttacagt acattttgaa tggtgaagat aaatatatgc    4020
attagatgta aaaggcgact cgaaagcttg gcgtaatcat ggtcatagct gtttcctgtg    4080
tgaaattgtt atccgctcac aattccacac aacatacgag ccggaagcat aaagtgtaaa    4140
gcctggggtg cctaatgagt gagctaactc acattaattg cgttgcgctc actgcccgct    4200
ttccagtcgg gaaacctgtc gtgccagctg cattaatgaa tcggccaacg cgcggggaga    4260
ggcggtttgc gtattgggcg ctcttccgct tcctcgctca ctgactcgct gcgctcggtc    4320
gttcggctgc ggcgagcggt atcagctcac tcaaaggcgg taatacggtt atccacagaa    4380
tcaggggata acgcaggaaa gaacatgtga gcaaaaggcc agcaaaaggc caggaaccgt    4440
aaaaaggccg cgttgctggc gttttccat aggctccgcc cccctgacga gcatcacaaa    4500
aatcgacgct caagtcagag gtggcgaaac ccgacaggac tataaagata ccaggcgttt    4560 cccccctggaa gctccctcgt gcgctctcct gttccgaccc tgccgcttac cggatacctg    4620
tccgcctttc tcccttcggg aagcgtggcg ctttctcaat gctcacgctg taggtatctc    4680
agttcggtgt aggtcgttcg ctccaagctg ggctgtgtgc acgaaccccc cgttcagccc    4740
gaccgctgcg ccttatccgg taactatcgt cttgagtcca acccggtaag acacgactta    4800
tcgccactgg cagcagccac tggtaacagg attagcagag cgaggtatgt aggcggtgct    4860
acagagttct tgaagtggtg gcctaactac ggctacacta aggacagt atttggtatc    4920 tgcgctctgc tgaagccagt taccttcgga aaaagagttg gtagctcttg atccggcaaa    4980
caaaccaccg ctggtagcgg tggtttttt gtttgcaagc agcagattac gcgcagaaaa    5040
aaaggatctc aagaagatcc tttgatcttt tctacgggt ctgacgctca gtggaacgaa    5100
aactcacgtt aagggatttt ggtcatgaga ttatcaaaaa ggatcttcac ctagatcctt    5160
ttaaattaaa aatgaagttt taaatcaatc taaagtatat atgagtaaac ttggcctgac    5220
agttaccaat gcttaatctg tgaggcacct atctcagcga tctgtctatt tcgttcatcc    5280
atagttgcct gactccccgt cgtgtagata actacgatac gggagggctt accatctggc    5340
cccagtgctg caatgatacc gcgagaccca cgctcaccgg ctccagattt atcagcaata    5400
aaccagccag ccggaagggc cgagcgcaga agtggtcctg caactttatc cgcctccatc    5460
cagtctatta attgttgccg ggaagctaga gtaagtagtt cgccagttaa tagtttgcgc    5520
aacgttgttg ccattgctac aggcatcgtg gtgtcacgct cgtcgtttgg tatggcttca    5580
ttcagctccg gttcccaacg atcaaggcga gttacatgat cccccatgtt gtgcaaaaaa    5640
gcggttagct ccttcggtcc tccgatcgtt gtcagaagta agttggccgc agtgttatca    5700
ctcatggtta tggcagcact gcataattct cttactgtca tgccatccgt aagatgcttt    5760
```

```
tctgtgactg gtgagtactc aaccaagtca ttctgagaat agtgtatgcg gcgaccgagt    5820
tgctcttgcc cggcgtcaat acgggataat accgcgccac atagcagaac tttaaaagtg    5880
ctcatcattg gaaaacgttc ttcggggcga aaactctcaa ggatcttacc gctgttgaga    5940
tccagttcga tgtaacccac tcgtgcaccc aactgatctt cagcatcttt tactttcacc    6000
agcgtttctg ggtgagcaaa aacaggaagg caaaatgccg caaaaaaggg aataagggcg    6060
acacggaaat gttgaatact catactcttc ctttttcaat attattgaag catttatcag    6120
ggttattgtc tcatgagcgg atacatattt gaatgtattt agaaaaataa acaaataggg    6180
gttccgcgca catttccccg aaaagtgcca cctgacgtct aagaaaccat tattatcatg    6240
acattaacct ataaaaatag gcgtatcacg aggccctttc gtc                       6283
```

<210> SEQ ID NO 6
<211> LENGTH: 756
<212> TYPE: DNA
<213> ORGANISM: artificial sequence
<220> FEATURE:
<223> OTHER INFORMATION: pAc6-LP-MCS-GPI vector with multiple cloning
      site with cloned GHR

<400> SEQUENCE: 6

```
caggatccat tttctggaag tgaggccaca gcagctatcc ttagcagagc accctggagt      60
ctgcaaagtg ttaatccagg cctaaagaca aattcttcta aggagcctaa attcaccaag     120
tgccgttcac ctgagcgaga gacttttttca tgccactgga cagatgaggt tcatcatggt    180
acaaagaacc taggacccat acagctgttc tataccagaa ggaacactca agaatggact    240
caagaatgga agaatgccc tgattatgtt tctgctgggg aaaacagctg ttactttaat     300
tcatcgttta cctccatctg gatacccttat tgtatcaagc taactagcaa tggtggtaca   360
gtggatgaaa agtgtttctc tgttgatgaa atagtgcaac cagatccacc cattgccctc    420
aactggactt tactgaacgt cagtttaact gggattcatg cagatatcca agtgagatgg    480
gaagcaccac gcaatgcaga tattcagaaa ggatggatgg ttctggagta tgaacttcaa    540
tacaaagaag taaatgaaac taatggaaa atgatgac ctatattgac aacatcagtt      600
ccagtgtact cattgaaagt ggataaggaa tatgaagtac gcgtgagatc caaacaacga    660
aactctggaa attatggcga gttcagtgag gtgctctatg taacacttcc tcagatgagc    720
caatttacat gtgaagaaga tttctaccga attcca                               756
```

<210> SEQ ID NO 7
<211> LENGTH: 897
<212> TYPE: DNA
<213> ORGANISM: artificial sequence
<220> FEATURE:
<223> OTHER INFORMATION: GHRGPI fusion nucleic acid sequence from
      pAc6GHRGPI

<400> SEQUENCE: 7

```
ttttctggaa gtgaggccac agcagctatc cttagcagag caccctggag tctgcaaagt     60
gttaatccag gcctaaagac aaattcttct aaggagccta aattcaccaa gtgccgttca    120
cctgagcgag agacttttttc atgccactgg acagatgagg ttcatcatgg tacaaagaac   180
ctaggaccca tacagctgtt ctataccaga aggaacactc aagaatggac tcaagaatgg    240 aagaatgcc ctgattatgt ttctgctggg gaaaacagct gttactttaa ttcatcgttt     300
acctccatct ggatacctta ttgtatcaag ctaactagca atggtggtac agtggatgaa    360
aagtgtttct ctgttgatga atagtgcaa ccagatccac ccattgccct caactggact    420
```

```
ttactgaacg tcagtttaac tgggattcat gcagatatcc aagtgagatg ggaagcacca    480
cgcaatgcag atattcagaa aggatggatg gttctggagt atgaacttca atacaaagaa    540
gtaaatgaaa ctaaatggaa aatgatggac cctatattga caacatcagt tccagtgtac    600
tcattgaaag tggataagga atatgaagta cgcgtgagat ccaaacaacg aaactctgga    660
aattatggcg agttcagtga ggtgctctat gtaacacttc ctcagatgag ccaatttaca    720
tgtgaagaag atttctaccg aattccatct ccaactccaa ctgaaacagc caccccatct    780
ccaactccaa aaccaaccag cacaccagaa gaaactgaag caccttcatc agcaacaact    840
cttatttcac cattatcttt aattgttatt ttcatttctt ttgttttatt aatttaa      897
```

<210> SEQ ID NO 8
<211> LENGTH: 298
<212> TYPE: PRT
<213> ORGANISM: artificial sequence
<220> FEATURE:
<223> OTHER INFORMATION: amino acid sequence from vector pAc6GHRGPI
      fusion protein

<400> SEQUENCE: 8

```
Phe Ser Gly Ser Glu Ala Thr Ala Ala Ile Leu Ser Arg Ala Pro Trp
1               5                   10                  15

Ser Leu Gln Ser Val Asn Pro Gly Leu Lys Thr Asn Ser Ser Lys Glu
            20                  25                  30

Pro Lys Phe Thr Lys Cys Arg Ser Pro Glu Arg Glu Thr Phe Ser Cys
        35                  40                  45

His Trp Thr Asp Glu Val His His Gly Thr Lys Asn Leu Gly Pro Ile
    50                  55                  60

Gln Leu Phe Tyr Thr Arg Arg Asn Thr Gln Glu Trp Thr Gln Glu Trp
65                  70                  75                  80

Lys Glu Cys Pro Asp Tyr Val Ser Ala Gly Glu Asn Ser Cys Tyr Phe
                85                  90                  95

Asn Ser Ser Phe Thr Ser Ile Trp Ile Pro Tyr Cys Ile Lys Leu Thr
            100                 105                 110

Ser Asn Gly Gly Thr Val Asp Glu Lys Cys Phe Ser Val Asp Glu Ile
        115                 120                 125

Val Gln Pro Asp Pro Pro Ile Ala Leu Asn Trp Thr Leu Leu Asn Val
    130                 135                 140

Ser Leu Thr Gly Ile His Ala Asp Ile Gln Val Arg Trp Glu Ala Pro
145                 150                 155                 160

Arg Asn Ala Asp Ile Gln Lys Gly Trp Met Val Leu Glu Tyr Glu Leu
                165                 170                 175

Gln Tyr Lys Glu Val Asn Glu Thr Lys Trp Lys Met Met Asp Pro Ile
            180                 185                 190

Leu Thr Thr Ser Val Pro Val Tyr Ser Leu Lys Val Asp Lys Glu Tyr
        195                 200                 205

Glu Val Arg Val Arg Ser Lys Gln Arg Asn Ser Gly Asn Tyr Gly Glu
    210                 215                 220

Phe Ser Glu Val Leu Tyr Val Thr Leu Pro Gln Met Ser Gln Phe Thr
225                 230                 235                 240

Cys Glu Glu Asp Phe Tyr Arg Ile Pro Ser Pro Thr Pro Thr Glu Thr
                245                 250                 255

Ala Thr Pro Ser Pro Thr Pro Lys Pro Thr Ser Thr Pro Glu Glu Thr
            260                 265                 270
```

```
Glu Ala Pro Ser Ser Ala Thr Thr Leu Ile Ser Pro Leu Ser Leu Ile
        275                 280                 285

Val Ile Phe Ile Ser Phe Val Leu Leu Ile
        290                 295

<210> SEQ ID NO 9
<211> LENGTH: 5155
<212> TYPE: DNA
<213> ORGANISM: artificial sequence
<220> FEATURE:
<223> OTHER INFORMATION: Vector pCR-3GPI_Thy-1 mammalian expression
      vector

<400> SEQUENCE: 9
```

| | | | | | |
|---|---|---|---|---|---|
| gcgcgcgttg | acattgatta | ttgactagtt | attaatagta | atcaattacg | gggtcattag     60 |
| ttcatagccc | atatatggag | ttccgcgtta | cataacttac | ggtaaatggc | ccgcctggct    120 |
| gaccgcccaa | cgaccccgc  | ccattgacgt | caataatgac | gtatgttccc | atagtaacgc    180 |
| caatagggac | tttccattga | cgtcaatggg | tggactattt | acggtaaact | gcccacttgg    240 |
| cagtacatca | agtgtatcat | atgccaagta | cgccccctat | tgacgtcaat | gacggtaaat    300 |
| ggcccgcctg | gcattatgcc | cagtacatga | ccttatggga | ctttcctact | tggcagtaca    360 |
| tctacgtatt | agtcatcgct | attaccatgg | tgatgcggtt | ttggcagtac | atcaatgggc    420 |
| gtggatagcg | gtttgactca | cggggatttc | caagtctcca | ccccattgac | gtcaatggga    480 |
| gtttgttttg | gcaccaaaat | caacgggact | ttccaaaatg | tcgtaacaac | tccgccccat    540 |
| tgacgcaaat | gggcggtagg | cgtgtacggt | gggaggtcta | tataagcaga | gctctctggc    600 |
| taactagaga | acccactgct | tactggctta | tcgaaattaa | tacgactcac | tatagggaga    660 |
| cccaagcttg | gtaccgagct | cggatccact | agtaacggcc | gccagtgtgc | tggaattctg    720 |
| cagatatcga | caagctggtc | aagtgtggcg | gcataagcct | gctggttcag | aacacatcct    780 |
| ggatgctgct | gctgctgctt | tccctctccc | tcctccaagc | cctagacttc | atttctctgt    840 |
| gactcgagca | tgcatctaga | gggcccttatt | ctatagtgtc | acctaaatgc | tagagctcgc    900 |
| tgatcagcct | cgactgtgcc | ttctagttgc | cagccatctg | ttgtttgccc | ctcccccgtg    960 |
| ccttccttga | ccctggaagg | tgccactccc | actgtccttt | cctaataaaa | tgaggaaatt   1020 |
| gcatcgcatt | gtctgagtag | gtgtcattct | attctggggg | gtggggtggg | gcaggacagc   1080 |
| aaggggagg  | attgggaaga | caatagcagg | catgctgggg | atgcggtggg | ctctatggct   1140 |
| tctgaggcgg | aaagaaccag | tggcggtaat | acgttatcc  | acagaatcag | ggataacgc    1200 |
| aggaaagaac | atgtgagcaa | aaggccagca | aaaggccagg | aaccgtaaaa | aggccgcgtt   1260 |
| gctggcgttt | ttccataggc | tccgcccccc | tgacgagcat | cacaaaaatc | gacgctcaag   1320 |
| tcagaggtgg | cgaaacccga | caggactata | aagataccag | gcgtttcccc | ctggaagctc   1380 |
| cctcgtgcgc | tctcctgttc | cgaccctgcc | gcttaccgga | tacctgtccg | cctttctccc   1440 |
| ttcgggaagc | gtggcgcttt | ctcatagctc | acgctgtagg | tatctcagtt | cggtgtaggt   1500 |
| cgttcgctcc | aagctgggct | gtgtgcacga | accccccgtt | cagcccgacc | gctgcgcctt   1560 |
| atccggtaac | tatcgtcttg | agtccaaccc | ggtaagacac | gacttatcgc | cactggcagc   1620 |
| agccactggt | aacaggatta | gcagagcgag | gtatgtaggc | ggtgctacag | agttcttgaa   1680 |
| gtggtggcct | aactacggct | acactagaag | gacagtattt | ggtatctgcg | ctctgctgaa   1740 |
| gccagttacc | ttcggaaaaa | gagttggtag | ctcttgatcc | ggcaaacaaa | ccaccgctgg   1800 |
| tagcggtggt | ttttttgttt | gcaagcagca | gattacgcgc | agaaaaaaag | gatctcaaga   1860 |

```
agatcctttg atcttttcta cggggtctga cgctcagtgg aacgaaaact cacgttaagg    1920
gattttggtc atgagattat caaaaaggat cttcacctag atccttttaa attaaaaatg    1980
aagttttaaa tcaatctaaa gtatatatga gtaacctgag gctatggcag ggcctgccgc    2040
cccgacgttg gctgcgagcc ctgggccttc acccgaactt gggggtggg gtggggaaaa    2100
ggaagaaacg cgggcgtatt ggccccaatg gggtctcggt ggggtatcga cagagtgcca    2160
gccctgggac cgaaccccgc gtttatgaac aaacgaccca acaccgtgcg ttttattctg    2220
tcttttatt gccgtcatag cgcgggttcc ttccggtatt gtctccttcc gtgtttcagt    2280
tagcctcccc ctagggtggg cgaagaactc cagcatgaga tccccgcgct ggaggatcat    2340
ccagccggcg tcccggaaaa cgattccgaa gcccaacctt tcatagaagg cggcggtgga    2400
atcgaaatct cgtgatggca ggttgggcgt cgcttggtcg gtcatttcga accccagagt    2460
cccgctcaga agaactcgtc aagaaggcga tagaaggcga tgcgctgcga atcgggagcg    2520
gcgataccgt aaagcacgag gaagcggtca gcccattcgc cgccaagctc ttcagcaata    2580
tcacgggtag ccaacgctat gtcctgatag cggtccgcca cacccagccg gccacagtcg    2640
atgaatccag aaaagcggcc attttccacc atgatattcg gcaagcaggc atcgccatgg    2700
gtcacgacga gatcctcgcc gtcgggcatg ctcgccttga gcctggcgaa cagttcggct    2760
ggcgcgagcc cctgatgctc ttgatcatcc tgatcgacaa gaccggcttc catccgagta    2820
cgtgctcgct cgatgcgatg tttcgcttgg tggtcgaatg ggcaggtagc cggatcaagc    2880
gtatgcagcc gccgcattgc atcagccatg atggatactt tctcggcagg agcaaggtga    2940
gatgacagga gatcctgccc cggcacttcg cccaatagca gccagtccct tcccgcttca    3000
gtgacaacgt cgagcacagc tgcgcaagga acgcccgtcg tggccagcca cgatagccgc    3060
gctgcctcgt cttgcagttc attcagggca ccggacaggt cggtcttgac aaaaagaacc    3120
gggcgcccct cgcgctgacag ccggaacacg cggcatcag agcagccgat tgtctgttgt    3180
gcccagtcat agccgaatag cctctccacc caagcggccg gagaacctgc gtgcaatcca    3240
tcttgttcaa tcatgcgaaa cgatcctcat cctgtctctt gatcgatctt tgcaaaagcc    3300
taggcctcca aaaagcctc ctcactactt ctggaatagc tcagaggccg aggcggcctc    3360
ggcctctgca taaataaaaa aaattagtca gccatggggc ggagaatggg cggaactggg    3420
cggagttagg ggcgggatgg gcggagttag gggcgggact atggttgctg actaattgag    3480
atgcatgctt tgcatacttc tgcctgctgg ggagcctggg gactttccac acctggttgc    3540
tgactaattg agatgcatgc tttgcatact tctgcctgct gggagcctg gggactttcc    3600
acacctaac tgacacacat tccacagctg gttctttccg cctcaggact cttccttttt    3660
caataaatca atctaaagta tatatgagta aacttggtct gacagttacc aatgcttaat    3720
cagtgaggca cctatctcag cgatctgtct atttcgttca tccatagttg cctgactccc    3780
cgtcgtgtag ataactacga tacgggaggg cttaccatct ggccccagtg ctgcaatgat    3840
accgcgagac ccacgctcac cggctccaga tttatcagca ataaaccagc cagccggaag    3900
ggccgagcgc agaagtggtc ctgcaacttt atccgcctcc atccagtcta ttaattgttg    3960
ccgggaagct agagtaagta gttcgccagt taatagtttg cgcaacgttg ttgccattgc    4020
tacaggcatc gtggtgtcac gctcgtcgtt tggtatggct tcattcagct ccggttccca    4080
acgatcaagg cgagttacat gatccccat gttgtgcaaa aaagcggtta gctccttcgg    4140
tcctccgatc gttgtcagaa gtaagttggc cgcagtgtta tcactcatgg ttatggcagc    4200
actgcataat tctcttactg tcatgccatc cgtaagatgc ttttctgtga ctggtgagta    4260
```

```
ctcaaccaag tcattctgag aatagtgtat gcggcgaccg agttgctctt gcccggcgtc    4320
aatacgggat aataccgcgc cacatagcag aactttaaaa gtgctcatca ttggaaaacg    4380
ttcttcgggg cgaaaactct caaggatctt accgctgttg agatccagtt cgatgtaacc    4440
cactcgtgca cccaactgat cttcagcatc ttttactttc accagcgttt ctgggtgagc    4500
aaaaacagga aggcaaaatg ccgcaaaaaa gggaataagg gcgacacgga aatgttgaat    4560
actcatactc ttcctttttc aatattattg aagcatttat cagggttatt gtctcatgag    4620
cggatacata tttgaatgta tttagaaaaa taaacaaata ggggttccgc gcacatttcc    4680
ccgaaaagtg ccacctgacg cgccctgtag cggcgcatta agcgcggcgg gtgtggtggt    4740
tacgcgcagc gtgaccgcta cacttgccag cgccctagcg cccgctcctt tcgctttctt    4800
cccttccttt ctcgccacgt tcgccggctt tccccgtcaa gctctaaatc ggggctccc    4860 tttagggttc cgatttagtg ctttacggca cctcgacccc aaaaaacttg attagggtga    4920
tggttcacgt agtgggccat cgccctgata acggttttt cgcccttga cgttggagtc    4980 cacgttcttt aatagtggac tcttgttcca aactggaaca acactcaacc ctatctcggt    5040
ctattctttt gatttataag ggattttgcc gatttcggcc tattggttaa aaaatgagct    5100
gatttaacaa aaatttaacg cgaattttaa caaaatatta acgcttacaa tttac        5155
```

<210> SEQ ID NO 10
<211> LENGTH: 962
<212> TYPE: DNA
<213> ORGANISM: Artificial sequence
<220> FEATURE:
<223> OTHER INFORMATION: pCR3GHRGPI, codes for GHRGPI anchor polypeptide in pCR-3GPI_Thy-1

<400> SEQUENCE: 10

```
taactagaga acccactgct tactggctta tcgaaattaa tacgactcac tatagggaga     60
cccaagcttg gtaccgagct cggatcctct agactcgagg tcctacaggt atggatctct    120
ggcagctgct gttgaccttg gcactggcag gatcaagtga tgcttttctct ggaagtgagg    180 ccacagcagc tatccttagc agagcaccct ggagtctgca aagtgttaat ccaggcctaa    240
agacaaattc ttctaaggag cctaaattca ccaagtgccg ttcacctgag cgagagactt    300
tttcatgcca ctggacagat gaggttcatc atggtacaaa gaacctagga cccatacagc    360
tgttctatac cagaaggaac actcaagaat ggactcaaga atggaaagaa tgccctgatt    420
atgtttctgc tggggaaaac agctgttact ttaattcatc gtttacctcc atctggatac    480
cttattgtat caagctaact agcaatggtg gtacagtgga tgaaaagtgt ttctctgttg    540
atgaaatagt gcaaccagat ccacccattg ccctcaactg gactttactg aacgtcagtt    600
taactgggat tcatgcagat atccaagtga gatgggaagc accacgcaat gcagatattc    660
agaaaggatg gatggttctg gagtatgaac ttcaatacaa agaagtaaat gaaactaaat    720
ggaaaatgat ggaccctata ttgacaacat cagttccagt gtactcattg aaagtggata    780
aggaatatga agtgcgtgtg agatccaaac aacgaaactc tggaaattat ggcgagttca    840
gtgaggtgct ctatgtaaca cttcctcaga tgagccaatt tacatgtgaa gaagatttct    900 acggaattc tgcagatatc gacaagctgg tcaagtgtgg cggcataagc ctgctggttc    960
ag                                                                  962
```

<210> SEQ ID NO 11
<211> LENGTH: 391

```
<212> TYPE: PRT
<213> ORGANISM: artificial sequence
<220> FEATURE:
<223> OTHER INFORMATION: mammalian GHRGPI anchor polypeptide in pCR-3GPI
      Thy-1 called pCR3GHRGPI

<400> SEQUENCE: 11
```

| | | | | | | | | | | | | | | |
|---|---|---|---|---|---|---|---|---|---|---|---|---|---|---|
| Arg | Ile | Leu | Thr | Arg | Gly | Pro | Thr | Gly | Met | Asp | Leu | Trp | Gln | Leu | Leu |
| 1 | | | | 5 | | | | | 10 | | | | | 15 |

Leu Thr Leu Ala Leu Ala Gly Ser Ser Asp Ala Phe Ser Gly Ser Glu
            20                  25                  30

Ala Thr Ala Ala Ile Leu Ser Arg Ala Pro Trp Ser Leu Gln Ser Val
        35                  40                  45

Asn Pro Gly Leu Lys Thr Asn Ser Ser Lys Glu Pro Lys Phe Thr Lys
50                  55                  60

Cys Arg Ser Pro Glu Arg Glu Thr Phe Ser Cys His Trp Thr Asp Glu
65                  70                  75                  80

Val His His Gly Thr Lys Asn Leu Gly Pro Ile Gln Leu Phe Tyr Thr
                85                  90                  95

Arg Arg Asn Thr Gln Glu Trp Thr Gln Glu Trp Lys Glu Cys Pro Asp
            100                 105                 110

Tyr Val Ser Ala Gly Glu Asn Ser Cys Tyr Phe Asn Ser Ser Phe Thr
        115                 120                 125

Ser Ile Trp Ile Pro Tyr Cys Ile Lys Leu Thr Ser Asn Gly Gly Thr
    130                 135                 140

Val Asp Glu Lys Cys Phe Ser Val Asp Glu Ile Val Gln Pro Asp Pro
145                 150                 155                 160

Pro Ile Ala Leu Asn Trp Thr Leu Leu Asn Val Ser Leu Thr Gly Ile
                165                 170                 175

His Ala Asp Ile Gln Val Arg Trp Glu Ala Pro Arg Asn Ala Asp Ile
            180                 185                 190

Gln Lys Gly Trp Met Val Leu Glu Tyr Glu Leu Gln Tyr Lys Glu Val
        195                 200                 205

Asn Glu Thr Lys Trp Lys Met Met Asp Pro Ile Leu Thr Thr Ser Val
    210                 215                 220

Pro Val Tyr Ser Leu Lys Val Asp Lys Glu Tyr Glu Val Arg Val Arg
225                 230                 235                 240

Ser Lys Gln Arg Asn Ser Gly Asn Tyr Gly Glu Phe Ser Glu Val Leu
                245                 250                 255

Tyr Val Thr Leu Pro Gln Met Ser Gln Phe Thr Cys Glu Glu Asp Phe
            260                 265                 270

Tyr Gly Asn Ser Ala Asp Ile Asp Lys Leu Val Lys Cys Gly Gly Ile
        275                 280                 285

Ser Leu Leu Val Gln Asn Thr Ser Trp Met Leu Leu Leu Leu Leu Ser
    290                 295                 300

Leu Ser Leu Leu Gln Ala Leu Asp Phe Ile Ser Leu Leu Glu His Ala
305                 310                 315                 320

Ser Arg Gly Pro Tyr Ser Ile Val Ser Pro Lys Cys Ser Ser Leu Ile
                325                 330                 335

Ser Leu Asp Cys Ala Phe Leu Pro Ala Ile Cys Cys Leu Pro Leu Pro
            340                 345                 350

Arg Ala Phe Leu Asp Pro Gly Arg Cys His Ser His Cys Pro Phe Leu
        355                 360                 365

Ile Lys Gly Asn Cys Ile Ala Leu Ser Glu Val Ser Phe Tyr Ser Gly
    370                 375                 380

Gly Trp Gly Gly Ala Gly Gln
385                 390

<210> SEQ ID NO 12
<211> LENGTH: 455
<212> TYPE: PRT
<213> ORGANISM: Homo sapiens

<400> SEQUENCE: 12

Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
                100                 105                 110

Glu Ile Ser Ser Cys Thr Val Asp Arg Asp Thr Val Cys Gly Cys Arg
            115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Thr Tyr Thr Pro Gly Asp Cys
290                 295                 300

Pro Asn Phe Ala Ala Pro Arg Arg Glu Val Ala Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro

```
                355             360             365
Leu Arg Trp Lys Glu Phe Val Arg Arg Leu Gly Leu Ser Asp His Glu
        370             375             380

Ile Asp Arg Leu Glu Leu Gln Asn Gly Arg Cys Leu Arg Glu Ala Gln
385             390             395             400

Tyr Ser Met Leu Ala Thr Trp Arg Arg Thr Pro Arg Arg Glu Ala
                405             410             415

Thr Leu Glu Leu Leu Gly Arg Val Leu Arg Asp Met Asp Leu Leu Gly
                420             425             430

Cys Leu Glu Asp Ile Glu Glu Ala Leu Cys Gly Pro Ala Ala Leu Pro
            435             440             445

Pro Ala Pro Ser Leu Leu Arg
    450             455

<210> SEQ ID NO 13
<211> LENGTH: 2161
<212> TYPE: DNA
<213> ORGANISM: Homo sapiens

<400> SEQUENCE: 13
cggcccagtg atcttgaacc ccaaaggcca gaactggagc ctcagtccag agaattctga      60
gaaaattaaa gcagagagga ggggagagat cactgggacc aggccgtgat ctctatgccc     120
gagtctcaac cctcaactgt caccccaagg cacttgggac gtcctggaca gaccgagtcc     180
cgggaagccc cagcactgcc gctgccacac tgccctgagc ccaaatgggg gagtgagagg     240
ccatagctgt ctggcatggg cctctccacc gtgcctgacc tgctgctgcc gctggtgctc     300
ctggagctgt tggtgggaat ataccctca ggggttattg gactggtccc tcacctaggg      360
gacagggaga agagagatag tgtgtgtccc caaggaaaat atatccaccc tcaaaataat     420
tcgatttgct gtaccaagtg ccacaaagga acctacttgt acaatgactg tccaggcccg     480
gggcaggata cggactgcag ggagtgtgag agcggctcct tcaccgcttc agaaaaccac     540
ctcagacact gcctcagctg ctccaaatgc gaaaggaaaa tgggtcaggt ggagatctct     600
tcttgcacag tggaccggga caccgtgtgt ggctgcagga agaaccagta ccggcattat     660
tggagtgaaa accttttcca gtgcttcaat tgcagcctct gcctcaatgg gaccgtgcac     720
ctctcctgcc aggagaaaca gaacaccgtg tgcacctgcc atgcaggttt ctttctaaga     780
gaaaacgagt gtgtctcctg tagtaactgt aagaaaagcc tggagtgcac gaagttgtgc     840
ctaccccaga ttgagaatgt taagggcact gaggactcag caccacagt gctgttgccc     900 ctggtcattt tctttggtct ttgccttta tccctcctct tcattggttt aatgtatcgc     960
taccaacggt ggaagtccaa gctctactcc attgtttgtg ggaaatcgac acctgaaaaa    1020
gagggggagc ttgaaggaac tactactaag cccctggccc caaacccaag cttcagtccc    1080
actccaggct tcacccccac cctgggcttc agtcccgtgc cagttccac cttcacctcc     1140 agctccacct ataccccgg tgactgtccc aactttgcgg ctccccgcag agaggtggca    1200 ccacccctatc aggggctga ccccatcctt gcgacagccc tcgcctccga ccccatcccc    1260 aaccccttc agaagtggga ggacagcgcc cacaagccac agagcctaga cactgatgac    1320
cccgcgacgc tgtacgccgt ggtggagaac gtgcccccgt gcgctggaa ggaattcgtg    1380 cggcgcctag ggctgagcga ccacgagatc gatcggctgg agctgcagaa cggcgctgc    1440 ctgcgcgagg cgcaatacag catgctggcg acctggagg cggcgcacgcc gcggcgagg    1500 gccacgctgg agctgctggg acgcgtgctc cgcgacatgg acctgctggg ctgcctggag    1560
```

-continued

```
gacatcgagg aggcgctttg cggccccgcc gccctcccgc ccgcgcccag tcttctcaga    1620
tgaggctgcg ccctgcggg cagctctaag gaccgtcctg cgagatcgcc ttccaacccc    1680
acttttttct ggaaaggagg ggtcctgcag gggcaagcag gagctagcag ccgcctactt    1740
ggtgctaacc cctcgatgta catagctttt ctcagctgcc tgcgcgccgc cgacagtcag    1800
cgctgtgcgc gcggagagag gtgcgccgtg ggctcaagag cctgagtggg tggtttgcga    1860
ggatgaggga cgctatgcct catgcccgtt tgggtgtcc tcaccagcaa ggctgctcgg    1920
gggcccctgg ttcgtccctg agccttttc acagtgcata agcagttttt tttgtttttg    1980
ttttgttttg ttttgttttt aaatcaatca tgttacacta atagaaactt ggcactcctg    2040
tgccctctgc ctggacaagc acatagcaag ctgaactgtc ctaaggcagg ggcgagcacg    2100
gaacaatggg gccttcagct ggagctgtgg acttttgtac atacactaaa attctgaagt    2160
t                                                                    2161
```

<210> SEQ ID NO 14
<211> LENGTH: 338
<212> TYPE: PRT
<213> ORGANISM: artificial sequence
<220> FEATURE:
<223> OTHER INFORMATION: TNF receptor type 1-GPI fusion polypeptide from vector pCR3TNFGPI

<400> SEQUENCE: 14

```
Arg Ile Leu Thr Arg Gly Pro Thr Gly Met Gly Leu Ser Thr Val Pro
1               5                   10                  15

Asp Leu Leu Leu Pro Leu Val Leu Leu Glu Leu Leu Val Gly Ile Tyr
            20                  25                  30

Pro Ser Gly Val Ile Gly Leu Val Pro His Leu Gly Asp Arg Glu Lys
        35                  40                  45

Arg Asp Ser Val Cys Pro Gln Gly Lys Tyr Ile His Pro Gln Asn Asn
    50                  55                  60

Ser Ile Cys Cys Thr Lys Cys His Lys Gly Thr Tyr Leu Tyr Asn Asp
65                  70                  75                  80

Cys Pro Gly Pro Gly Gln Asp Thr Asp Cys Arg Glu Cys Glu Ser Gly
                85                  90                  95

Ser Phe Thr Ala Ser Glu Asn His Leu Arg His Cys Leu Ser Cys Ser
            100                 105                 110

Lys Cys Arg Lys Glu Met Gly Gln Val Glu Ile Ser Ser Cys Thr Val
        115                 120                 125

Asp Arg Asp Thr Val Cys Gly Cys Arg Lys Asn Gln Tyr Arg His Tyr
    130                 135                 140

Trp Ser Glu Asn Leu Phe Gln Cys Phe Asn Cys Ser Leu Cys Leu Asn
145                 150                 155                 160

Gly Thr Val His Leu Ser Cys Gln Glu Lys Gln Asn Thr Val Cys Thr
                165                 170                 175

Cys His Ala Gly Phe Phe Leu Arg Glu Asn Glu Cys Val Ser Cys Ser
            180                 185                 190

Asn Cys Lys Lys Ser Leu Glu Cys Thr Lys Leu Cys Leu Pro Gln Ile
        195                 200                 205

Glu Asn Val Lys Gly Thr Glu Asp Ser Gly Thr Thr Gly Asn Ser Ala
    210                 215                 220

Asp Ile Asp Lys Leu Val Lys Cys Gly Gly Ile Ser Leu Leu Val Gln
225                 230                 235                 240
```

```
Asn Thr Ser Trp Met Leu Leu Leu Leu Ser Leu Ser Leu Leu Gln
                245                 250                 255

Ala Leu Asp Phe Ile Ser Leu Leu Glu His Ala Ser Arg Gly Pro Tyr
            260                 265                 270

Ser Ile Val Ser Pro Lys Cys Ser Ser Leu Ile Ser Leu Asp Cys Ala
                275                 280                 285

Phe Leu Pro Ala Ile Cys Cys Leu Pro Leu Pro Arg Ala Phe Leu Asp
        290                 295                 300

Pro Gly Arg Cys His Ser His Cys Pro Phe Leu Ile Lys Gly Asn Cys
305                 310                 315                 320

Ile Ala Leu Ser Glu Val Ser Phe Tyr Ser Gly Gly Trp Gly Gly Ala
                325                 330                 335

Gly Gln

<210> SEQ ID NO 15
<211> LENGTH: 925
<212> TYPE: PRT
<213> ORGANISM: artificial sequence
<220> FEATURE:
<223> OTHER INFORMATION: leptin receptor-GPI fusion from Vector
      pCR3ObRGPI fusion protein

<400> SEQUENCE: 15

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255
```

```
Trp Ser Ser Pro Pro Leu Val Pro Phe Pro Leu Gln Tyr Gln Val Lys
            260             265             270

Tyr Ser Glu Asn Ser Thr Thr Val Ile Arg Glu Ala Asp Lys Ile Val
        275             280             285

Ser Ala Thr Ser Leu Leu Val Asp Ser Ile Leu Pro Gly Ser Ser Tyr
    290             295             300

Glu Val Gln Val Arg Gly Lys Arg Leu Asp Gly Pro Gly Ile Trp Ser
305             310             315             320

Asp Trp Ser Thr Pro Arg Val Phe Thr Thr Gln Asp Val Ile Tyr Phe
                325             330             335

Pro Pro Lys Ile Leu Thr Ser Val Gly Ser Asn Val Ser Phe His Cys
            340             345             350

Ile Tyr Lys Lys Glu Asn Lys Ile Val Pro Ser Lys Glu Ile Val Trp
        355             360             365

Trp Met Asn Leu Ala Glu Lys Ile Pro Gln Ser Gln Tyr Asp Val Val
    370             375             380

Ser Asp His Val Ser Lys Val Thr Phe Phe Asn Leu Asn Glu Thr Lys
385             390             395             400

Pro Arg Gly Lys Phe Thr Tyr Asp Ala Val Tyr Cys Cys Asn Glu His
                405             410             415

Glu Cys His His Arg Tyr Ala Glu Leu Tyr Val Ile Asp Val Asn Ile
            420             425             430

Asn Ile Ser Cys Glu Thr Asp Gly Tyr Leu Thr Lys Met Thr Cys Arg
        435             440             445

Trp Ser Thr Ser Thr Ile Gln Ser Leu Ala Glu Ser Thr Leu Gln Leu
    450             455             460

Arg Tyr His Arg Ser Ser Leu Tyr Cys Ser Asp Ile Pro Ser Ile His
465             470             475             480

Pro Ile Ser Glu Pro Lys Asp Cys Tyr Leu Gln Ser Asp Gly Phe Tyr
                485             490             495

Glu Cys Ile Phe Gln Pro Ile Phe Leu Leu Ser Gly Tyr Thr Met Trp
            500             505             510

Ile Arg Ile Asn His Ser Leu Gly Ser Leu Asp Ser Pro Pro Thr Cys
        515             520             525

Val Leu Pro Asp Ser Val Val Lys Pro Leu Pro Pro Ser Ser Val Lys
    530             535             540

Ala Glu Ile Thr Ile Asn Ile Gly Leu Leu Lys Ile Ser Trp Glu Lys
545             550             555             560

Pro Val Phe Pro Glu Asn Asn Leu Gln Phe Gln Ile Arg Tyr Gly Leu
                565             570             575

Ser Gly Lys Glu Val Gln Trp Lys Met Tyr Glu Val Tyr Asp Ala Lys
            580             585             590

Ser Lys Ser Val Ser Leu Pro Val Pro Asp Leu Cys Ala Val Tyr Ala
        595             600             605

Val Gln Val Arg Cys Lys Arg Leu Asp Gly Leu Gly Tyr Trp Ser Asn
    610             615             620

Trp Ser Asn Pro Ala Tyr Thr Val Val Met Asp Ile Lys Val Pro Met
625             630             635             640

Arg Gly Pro Glu Phe Trp Arg Ile Ile Asn Gly Asp Thr Met Lys Lys
                645             650             655

Glu Lys Asn Val Thr Leu Leu Trp Lys Pro Leu Met Lys Asn Asp Ser
            660             665             670

Leu Cys Ser Val Gln Arg Tyr Val Ile Asn His His Thr Ser Cys Asn
```

-continued

```
                    675                 680                 685
Gly Thr Trp Ser Glu Asp Val Gly Asn His Thr Lys Phe Thr Phe Leu
    690                 695                 700
Trp Thr Glu Gln Ala His Thr Val Thr Val Leu Ala Ile Asn Ser Ile
705                 710                 715                 720
Gly Ala Ser Val Ala Asn Phe Asn Leu Thr Phe Ser Trp Pro Met Ser
                725                 730                 735
Lys Val Asn Ile Val Gln Ser Leu Ser Ala Tyr Pro Leu Asn Ser Ser
            740                 745                 750
Cys Val Ile Val Ser Trp Ile Leu Ser Pro Ser Asp Tyr Lys Leu Met
            755                 760                 765
Tyr Phe Ile Ile Glu Trp Lys Asn Leu Asn Glu Asp Gly Glu Ile Lys
    770                 775                 780
Trp Leu Arg Ile Ser Ser Ser Val Lys Lys Tyr Tyr Ile His Asp His
785                 790                 795                 800
Phe Ile Pro Ile Glu Lys Tyr Gln Phe Ser Leu Tyr Pro Ile Phe Met
                805                 810                 815
Glu Gly Val Gly Lys Pro Lys Ile Ile Asn Ser Phe Thr Gln Asp Asp
            820                 825                 830
Ile Glu Lys His Gln Ser Gly Asn Ser Ala Asp Ile Asp Lys Leu Val
            835                 840                 845
Lys Cys Gly Gly Ile Ser Leu Leu Val Gln Asn Thr Ser Trp Met Leu
    850                 855                 860
Leu Leu Leu Leu Ser Leu Ser Leu Leu Gln Ala Leu Asp Phe Ile Ser
865                 870                 875                 880
Leu Leu Glu His Ala Ser Arg Gly Pro Tyr Ser Ile Val Ser Pro Lys
                885                 890                 895
Cys Ser Ser Leu Ile Ser Leu Asp Cys Ala Phe Leu Pro Ala Ile Cys
                900                 905                 910
Cys Leu Pro Leu Pro Arg Ala Phe Leu Asp Pro Gly Arg
            915                 920                 925
```